US006436871B1

United States Patent
Liu

(10) Patent No.: US 6,436,871 B1
(45) Date of Patent: Aug. 20, 2002

(54) CATALYSTS FOR OXIDATIVE DEHYDROGENATION

(75) Inventor: Yumin Liu, Santa Clara, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/255,384

(22) Filed: Feb. 22, 1999

(51) Int. Cl.[7] .......................... B01J 23/00; B01J 23/40; B01J 23/58; B01J 23/56; B01J 23/70
(52) U.S. Cl. ..................... 502/335; 502/325; 502/326; 502/327; 502/328; 502/330; 502/332; 502/337; 502/338; 423/594
(58) Field of Search ............................ 502/325, 326, 502/327, 328, 330, 332, 335, 337, 338, 353; 423/594

(56) References Cited

U.S. PATENT DOCUMENTS

| | | | |
|---|---|---|---|
| 3,678,124 A | 7/1972 | Stepanov et al. | 260/680 E |
| 3,832,205 A | 8/1974 | Lowery | 106/288 |
| 3,862,256 A | 1/1975 | Isailingold et al. | 260/680 E |
| 4,115,441 A | * 9/1978 | Shaw et al. | 562/534 |
| 4,143,120 A | * 3/1979 | Sermon | 423/239 |
| 4,176,140 A | 11/1979 | Bertus et al. | 585/629 |
| 4,250,346 A | 2/1981 | Young et al. | 585/658 |
| 4,283,307 A | * 8/1981 | Barone et al. | 252/432 |
| 4,296,607 A | 10/1981 | Lawless | 62/6 |
| 4,524,236 A | 6/1985 | McCain | 585/658 |

(List continued on next page.)

FOREIGN PATENT DOCUMENTS

| | | | |
|---|---|---|---|
| EP | 0 573 713 A1 | 6/1992 | |
| EP | 0 544 372 A1 | 11/1992 | |
| EP | 661 254 A3 | 7/1995 | C07C/5/48 |
| EP | 661 254 A2 | 7/1995 | C07C/5/48 |
| WO | WO 96/33149 | 10/1996 | |
| WO | WO 99/42404 | 8/1999 | C01G/51/00 |

OTHER PUBLICATIONS

Zhang, Mingqian, et al., "Calcium–nickel–lithium oxide: A high selectivity catalyst for the oxidative dehydrogenation of ethane to ethylene," J. Chem. Soc., Chem. Commun., pp. 1480–1481, 1993.

Ducarme, V., et al., "Low temperature oxidative dehydrogenation of ethane over Ni–based catalysts," Catalyst Letters 23, pp. 97–101, 1994.

López, R. Juárez, et al., "Oxidative dehydrogenation of ethane on supported vanadium–containing oxides," Applied Catalysis A: General 124, pp. 281–296, 1995.

Ducarme, V., et al., "Low temperature oxidative dehydrogenation of ethane over new catalysts based on group VIII metals," presented before the Division of Petroleum Chemistry, Inc., 211th National Meeting, American Chemistry Society, New Orleans, Louisiana, Mar. 24–29, 1996.

Ji, Lang, et al, "Effect of group VIII elements on the behavior of Li/CaO catalyst in the oxidative dehydrogenation of ethane," React. Kinet. Catal. Lett., vol. 62, No. 1, 121–128, 1997.

(List continued on next page.)

Primary Examiner—Steven P. Griffin
Assistant Examiner—Cam N. Nguyen
(74) Attorney, Agent, or Firm—Pennie & Edmonds LLP

(57) ABSTRACT

Catalysts for oxidative dehydrogenation of alkane to one or more olefins, exemplified by ethane to ethylene, are disclosed. The catalyst comprises a mixture of metal oxides having as an important component nickel oxide (NiO) and gives high conversion and selectivity. For example, the catalyst can be used to make ethylene by contacting it with a gas mixture containing ethane and oxygen. The gas mixture may optionally contain ethylene, an inert diluent such as nitrogen, or both ethylene and an inert diluent.

37 Claims, 2 Drawing Sheets

U.S. PATENT DOCUMENTS

| | | | | |
|---|---|---|---|---|
| 4,568,790 A | | 2/1986 | McCain | 585/658 |
| 4,709,071 A | * | 11/1987 | Sasaki et al. | 558/322 |
| 4,788,371 A | | 11/1988 | Imai et al. | 585/443 |
| 4,836,117 A | * | 6/1989 | Teller et al. | 110/342 |
| 4,940,826 A | | 7/1990 | Font Freide et al. | 585/600 |
| 4,959,339 A | * | 9/1990 | Arai | 502/302 |
| 4,996,387 A | | 2/1991 | Gerhold et al. | 585/654 |
| 5,053,577 A | * | 10/1991 | Teller et al. | 585/500 |
| 5,094,990 A | * | 3/1992 | Sasaki et al. | 502/214 |
| 5,132,269 A | * | 7/1992 | Sasaki et al. | 502/205 |
| 5,210,293 A | | 5/1993 | Kitson | 562/512.2 |
| 5,219,816 A | | 6/1993 | Zhou et al. | 502/223 |
| 5,376,613 A | | 12/1994 | Dellinger et al. | 502/304 |
| 5,439,859 A | | 8/1995 | Durante et al. | 502/66 |
| 5,593,935 A | | 1/1997 | Golunski et al. | 502/339 |
| 5,723,707 A | | 3/1998 | Heyse et al. | 585/444 |
| 5,733,518 A | | 3/1998 | Durante et al. | 423/248 |
| 5,759,946 A | | 6/1998 | Hoang et al. | 502/303 |
| 5,780,700 A | | 7/1998 | Hagemeyer et al. | 585/617 |
| 5,834,394 A | * | 11/1998 | Chen et al. | 502/302 |
| 6,028,220 A | * | 2/2000 | Wada et al. | 562/546 |
| 6,063,491 A | * | 5/2000 | Fujikata et al. | 428/332 |
| 6,080,893 A | * | 6/2000 | Hecquet et al. | 568/479 |
| 6,251,821 B1 | * | 6/2000 | Hecquet et al. | 502/306 |
| 2001/0005769 A1 | * | 6/2001 | Rao et al. | 568/804 |

OTHER PUBLICATIONS

Schuurman, Y., et al., "Low temperature oxidative dehydrogenation of ethane over catalysts based on group VIII metals," *Applied Catalysis: General 163,* pp. 227–235, 1997.

Ducarme, V., et al., "Oxidative dehydrogenation of ethane of low temperature over nickel catalysts: Influence of morphology and chemical state of the solid during reaction," in *Natural Gas Conversion IV. Studies in Surface Science and Catalysis,* vol. 107, (Eds. M. de Pontes, R.L. Espinoza, J.H. Scholz and M.S. Scurrell), pp. 361–366, 1997.

Barrault, J., et al., "Selective oxidation of propane into oxygenated compounds over promoted nickel–molybdenum catalysts," in $3^{rd}$ *World Congress on Oxidation Catalysis,* (Eds. R.K. Grasselli, S.T. Oyama, A.M. Gaffney and J.E. Lyons) pp. 375–382, 1997.

Jalowiecki–Duhamel, L., et al., "Oxidative dehydrogenation of propane on $CeNi_xO_y$ ($0 \leq x \leq 1$) mixed oxides hydrogen acceptors," in $3^{rd}$ *World Congress on Oxidation Catalysis,* (Eds. R. K. Grasselli, S.T. Oyama, A.M. Gaffney and J.E. Lyons), pp. 383–392, 1997.

* cited by examiner

CATALYSTS FOR OXIDATIVE DEHYDROGENATION

This application is related to U.S. patent application Ser. No. 09/255,371, filed on Feb. 22, 1999, U.S. Pat. No. 6,355,854 issued Mar. 12, 2000, and incorporated herein by reference.

BACKGROUND OF THE INVENTION

1. Field of the Invention

This invention relates to methods and materials for the dehydrogenation of alkanes, particularly the conversion of ethane to ethylene, and more particularly, to mixed oxide catalysts for oxidative dehydrogenation of ethane.

2. Background of the Invention

Ethylene can be produced by thermal cracking of hydrocarbons, and by nonoxidative dehydrogenation or oxidative dehydrogenation of ethane (ODHE). The latter process is attractive for many reasons. For example, compared to thermal cracking, high ethane conversion can be achieved at relatively low temperatures (about 400° C. or below). Unlike thermal cracking, catalytic ODHE is exothermic, requiring no additional heat to sustain reaction. Furthermore, in contrast to catalytic dehydrogenation, catalyst deactivation by coke formation should be minimal in ODHE because of the presence of oxygen in the reactor feed. Other alkanes can similarly be oxidatively dehydrogenated.

In the late seventies, Thorsteinson and coworkers first disclosed useful low temperature ODHE catalysts comprised of mixed oxides containing molybdenum, vanadium, and a third transition metal. E. M Thorsteinson et al., "The Oxidative Dehydrogenation of Ethane over Catalyst Containing Mixed oxide of Molybdenum and Vanadium," 52 *J. Catalysis* 116–32 (1978). Later studies examined families of alumina-supported vanadium-containing oxide catalysts, MV and MVSb, where M is Ni, Co, Bi, and Sn. R. Juarez Lopez et al., "Oxidative Dehydrogenation of Ethane on Supported Vanadium-Containing Oxides," 124 *Applied Catalysis A: General* 281–96 (1995). More recently, Schuurman and coworkers describe unsupported iron, cobalt and nickel oxide catalysts that are active in ODHE. Y. Schuurman et al., "Low Temperature Oxidative Dehydrogenation of Ethane over Catalysts Based on Group VIII Metals," 163 *Applied Catalysis A: General* 227–35 (1997). Although the mixed oxide catalysts reported by Thorsteinson, Schuurman and others might be useful discoveries, they represent a small fraction of potentially active inorganic oxide mixtures.

Industrial interest has stimulated investigations into new catalysts and methods for improved performance (e.g., conversion and selectivity) for the oxidative dehydrogenation of alkanes. There is a need for new dehydrogenation catalysts and methods.

SUMMARY OF THE INVENTION

This invention discloses catalysts and methods for the oxidative dehydrogenation of alkanes that have from 2 to 4 carbon atoms and particularly ethane to ethylene. These catalysts primarily include nickel oxide and catalyze oxidative dehydrogenation with conversions of greater than 5% and with selectivity of greater than 70%. An object of the present invention is to provide a process whereby a $C_2$–$C_4$ alkane can be oxidatively dehydrogenated to one or more olefins with relatively high levels of conversion and selectivity. A further object of this invention is to provide a catalyst that selectively catalyzes the reaction of a $C_2$–$C_4$ alkane with oxygen to produce one or more corresponding $C_2$–$C_4$ olefins with relatively high levels of conversion and selectivity, meaning preferably without the concurrent production of significant amounts of by-products, such as carbon monoxide or carbon dioxide.

In general, the catalysts of this invention have as a required component nickel oxide and it is an object of this invention to provide a catalyst for the oxidative dehydrogenation of an alkane into one or more olefins having nickel oxide (NiO). The nickel oxide is combined with other metal oxides, dopants, carriers, binders and/or fillers into a catalyst that is contacted with a gas mixture. The gas mixture comprises at least the alkane and oxygen, but may also include diluents (such as argon, nitrogen, etc.) or other components (such as water or carbon dioxide). Optionally, the gas mixture that contacts the catalyst may also include one or more of the olefin products for an oxidative dehydrogenation process that converts a gas mixture having one ratio of alkane to alkene to a gas mixture having a different ratio of alkane to alkene. The catalysts of this invention include a material or composition of matter having the empirical formula:

$$Ni_x A_j B_k C_l O_i \qquad \text{I}$$

wherein

Ni is nickel and x is in the range of about 0.1–0.96;

A is selected from the group consisting of Nb, Ta, Co and combinations thereof and j is in the range of from about 0–0.8;

B is an element selected from the group consisting of alkali metals, alkaline earths, or lanthanides and combinations thereof, including Li, Na, K, Rb, Cs, Mg, Ca, Sr, Ba, Mn, La, Ce, Pr, Nd, Sm and combinations thereof and k is in the range of from 0–0.5;

C is an element selected from the group consisting of Sn, Al, Fe, Si, B, Sb, Tl, In, Ge, Cr, Pb and combinations thereof and l is in the range of from 0–0.5;

i is a number that satisfies the valence requirements of the other elements present; and the sum of j, k and l is at least 0.04.

DETAILED DESCRIPTION OF THE INVENTION

Figure 1:
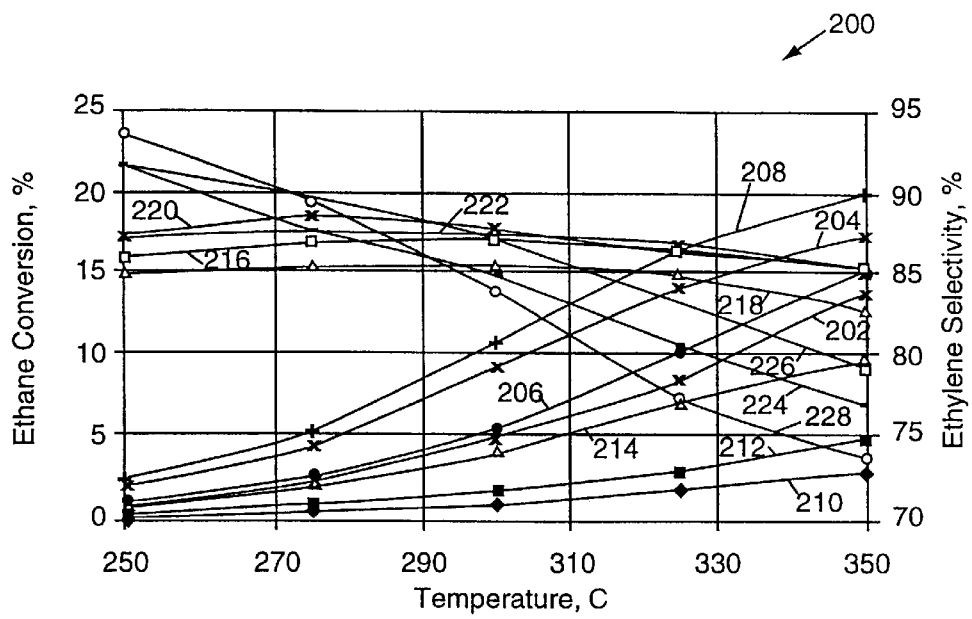
FIG. 1 shows ethane conversion and ethylene selectivity as a function of reaction temperature for Ni—Nb oxide mixtures and for an optimized Mo—V—Nb catalyst.

The present invention includes nickel oxide catalysts for oxidative dehydrogenation of alkanes having 2, 3 or 4 carbon atoms to the corresponding olefin(s). The invention is exemplified for ethane to ethylene. An important feature of this invention is the relatively high percentages of conversion and selectivity that the catalyst provides for a dehydrogenation process. As used herein the phrase selectivity (also known as efficiency) refers to a percentage that reflects the amount of desired olefin product produced as compared to the total carbon products as follows:

$$\% \text{ selectivity} = 100 \times \frac{\text{Moles of alkene produced}}{\text{The molar alkene-equivalent sum (carbon basis) of all carbon-containing products, excluding the alkane in the effluent}}.$$

Similarly as used herein the term conversion refers to a percentage that reflects the amount of alkane provided to the reaction as compared to the total carbon products as follows:

$$\% \text{ conversion} = 100 \times \frac{\text{The molar alkane-equivalent sum (carbon basis) of all carbon-containing products, excluding the alkane in the effluent}}{\text{Moles of alkane in the reaction mixture, which is fed to the catalyst in the reactor}}.$$

These expressions are the theoretical expressions for selectivity and conversion. Simplified formulas have been used in the examples herein, and may be used by those of skill in the art. The simplified formula for % selectivity is % selectivity=100×[(moles of alkene)/(moles of alkene+((moles of carbon dioxide)/2))]. Similarly the simplified formula for % conversion is % conversion=100×[(moles of alkene+((moles of carbon dioxide)/2))/(moles of alkane)]. Although these simplified formulas are used, typically the only products observed in the ethane to ethylene oxidative dehydrogenation reaction (using an ethane and oxygen gas feed) are ethylene and carbon dioxide. In these formulas, those of skill in the art will recognize that an alkene is an olefin. These calculations are straightforward when ethane and propane are the alkanes. When butane is the alkane, the possibility exists that the product is one or more of 1-butene, 2-butenes or 1,3-butadiene. Thus, the percentages for selectivity and conversion are percentages of one or more of these dehydrogenated products of butane. Using the catalysts and process that are disclosed herein, selectivity of dehydrogenation of alkane to the corresponding olefin can be greater than 70%, 75%, 80%, 85% and most preferably greater than 90%. Also, the conversion can be greater than 5% and preferably greater than 10% or greater than 15%. In fact, the conversions may be 20% or greater. Surprisingly, the experimental results suggest that the selectivity does not alter significantly with the conversion, meaning that within experimental error the selectivity is more or less independent of the conversion.

The catalysts of this invention include a composition of matter or material having the empirical formula:

$$\text{Ni}_x\text{A}_j\text{B}_k\text{C}_l\text{O}_i \qquad \qquad \text{I}$$

wherein

Ni is nickel and x is in the range of about 0.1–0.96;

A is selected from the group consisting of Nb, Ta, Co and combinations thereof and j is in the range of from about 0–0.8;

B is an element selected from the group consisting of alkali metals, alkaline earths, or lanthanides and combinations thereof, including Li, Na, K, Rb, Cs, Mg, Ca, Sr, Ba, Mn, La, Ce, Pr, Nd, Sm and combinations thereof and k is in the range of from 0–0.5;

C is an element selected from the group consisting of Sn, Al, Fe, Si, B, Sb, Tl, In, Ge, Cr, Pb and combinations thereof and l is in the range of from 0–0.5 i is a number that satisfies the valence requirements of the other elements present; and the sum of j, k and l is at least 0.04.

Catalysts defined by this formula include nickel that is substantially in the oxidized state; meaning that there may be nickel metal present, but it will not be the majority. Nickel oxide (NiO) is present in an amount preferably of at least 20% by weight, more preferably at least 50% by weight and most preferable at least 60% by weight. In some preferred embodiments, Nb and Ta are included together in the composition (with Co being optional) and j may range from about 0.05–0.8. Generally, x may range from about 0.1–0.96 (e.g., 10–96%), preferably from about 0.3 to about 0.85, more preferably from about 0.5 to about 0.8 and most preferably from about 0.6 to about 0.8. Generally, j may range from about 0 to about 0.8 (e.g., 0–80%), but preferably ranges from 0.04 to about 0.5, more preferably from about 0.04 to 0.4 and alternatively from about 0.3 to about 0.4. Generally, k and l each may range from about 0 to about 0.5 (e.g., 0–50%), but preferably ranges from 0 to about 0.4, more preferably from about 0 to 0.1 and most preferably from about 0 to about 0.05. Within these ranges, the sum of j, k and l will be at least about 0.04 but may range as high as about 0.9. In other embodiments, the sum of j, k and l will be no more than 0.5, 0.4 and optionally 0.3. In some embodiments, Nb and Ta are included together in the composition (with Co being optional) and j may range from about 0.04 to about 0.8 or in any of the other listed ranges for j.

In still other embodiments, the catalysts can be represented by the empirical formula:

$$\text{Ni}_a\text{Co}_b\text{Nb}_c\text{Ta}_d\text{Sn}_e\text{K}_f\text{Al}_g\text{Fe}_h\text{O}_i. \qquad \qquad \text{II}$$

In formula II, subscripts b, c and d are numbers greater than or equal to zero but less than one. At least one of b, c and d is nonzero. Subscripts e and f are numbers greater than or equal to zero but less than or equal to about 0.35; subscripts g and h are numbers greater than or equal to zero but less than or equal to about 0.10; and subscript a is a number greater than zero but less than one, and satisfies the expression:

$$a \leq 1-b-c-d-e-f-g-h. \qquad \qquad \text{III}$$

In equation II, subscript i is a number that satisfies valence requirements of elements listed in the formula.

The catalyst is supplied to the reactor as a fixed bed—the catalyst may or may not be supported on a carrier. If a carrier is used, the carrier may be selected from the group consisting of alumina, silica, titania, zirconia, magnesia, zeolites, clays or mixtures thereof. The catalyst may take any form, including powder, split, granular, pellets or a shaped catalyst, such as tablets, rings, cylinders, stars, ripped bodies, extrudates, etc. known to those of skill in the art. For example, the shaping of the mixture of starting composition may be carried out by compaction (for example tableting or extrusion) with or without a prior kneading step, if necessary with addition of conventional auxiliaries, for example graphite or stearic acid or its salts as lubricants. In the case of unsupported catalysts, the compaction gives the desired catalyst geometry directly. Hollow cylinders may have an external diameter and length of from 2 to 10 mm and a wall thickness of from 1 to 3 mm. Very generally, the mixture of starting composition metal may be shaped either before or after the calcination. This can also be carried out, for example, by comminuting the mixture after the calcination and applying it to inert supports to produce coated catalysts. However, the application can also be carried out before the final calcination. The catalyst may be diluted (e.g., have its density reduced) with binders and/or inert fillers, which are known to those of skill in the art, including for example quartz chips, sand or cement. Diluents may be added to the catalyst in the range of from about 0 to about 30% by volume, preferably in the range of from about 10 to about 25% by volume. Preferred diluents improve the heat removal or heat transfer of the catalyst to help avoid hot spots or to modify hot spots. Binders generally provide mechanical strength to the catalyst and may be added in the range of from about 0–30% by volume, preferably in the range of from about 5 to about 25% by volume. Useful binders include silica sol, silica, alumina, diamateous earth, hydrated zirconia, silica aluminas, alumina phosphates, naturally occurring materials and cement and combinations thereof. See, e.g., the discussion of supports, shapes, binders and fillers in U.S. Pat. Nos. 5,376,613, 5,780,700 and 4,250,346, each of which is incorporated herein by reference for all purposes. The percentages or amounts of binders, fillers or organics referred to herein relate to the starting ingredients prior to calcination. Thus, the above is not intended to imply statements on the actual bonding ratios, to which the invention is not restricted; for example during calcination other phases can form.

The disclosed mixed oxides can be used to make an olefin from the respective alkane, for example, ethylene from ethane, by contacting them, in a pressure vessel or reactor, with a gas mixture comprised of the alkane and oxygen. Contact between the catalyst and the gas mixture occurs by passing the gas mixture through the interstices in the fixed bed, which ensures intimate contact between the gas mixture and the catalyst. Also, the gas mixture may be passed over the catalyst surface, in situations were gas cannot pass through the catalyst. During contact, the catalyst and the gas mixture are maintained at a temperature between about 250° C. and 400° C., thus the reaction temperature is typically 400° C. or less, preferably 325° C. or less and alternatively 300° C. or less. The reaction pressure during contacting can range from about 0.5 to 20 bar and for a time of between 100 milliseconds to about 10 seconds. Generally, the gas mixture that contacts the catalyst comprises the alkane to be dehydrogenated and oxygen or an oxygen source in the reactor. The gas mixture may also include diluents such as nitrogen, argon or carbon dioxide. In other embodiments, the gas mixture may also include water (e.g., steam) or butylenes or ethylene or propylene.

The disclosed catalyst can convert alkane to olefin (e.g., ethane to ethylene) even in the presence of significant amounts of olefin (e.g., ethylene) in the reactor feed. Typically the gas mixture that is contacted with the catalyst has an oxygen content in the range of from about 0.01 to about 50% by volume and the alkane in the range of from about 5–99.99% by volume. A preferred range includes 0.01 to 20% by volume of oxygen and 10 to 90% by volume of alkane (e.g., ethane, propane or butane). In an alternative embodiment, the gas mixture can further include the olefin of the corresponding alkane that is being dehydrogenated. For example, an ethane gas feed may also contain ethylene, such that the catalyst and methods of this invention will convert such a gas stream to a more olefin rich content. For example, a 70%/30% by volume ethane/ethylene reactant gas can be converted to a 60%/40% by volume ethane/ethylene product or a 50%/50% by volume ethane/ethylene product. Generally, mixed gas reactant streams may have an alkane/olefin range from about 99%/1% by volume to about 50%/50% by volume. In another alternative, the gas mixture that contacts the catalyst may contain raffinate II, which is a mixture of butane, 2-butenes and 1-butene. Because of the ability of these catalysts to perform the desired dehydrogenation selectively, mixed streams may be converted into more uniform streams.

Generally, the catalyst can be prepared by sol-gel, freeze drying, spray drying, precipitation, impregnation, incipient wetness, spray impregnation, ion exchange, wet mix/evaporation, dry mix/compacting, high coating, fluid bed coating, bead coating, spin coating, physical vapor deposition (sputtering, electron beam evaporation, laser ablation) and chemical vapor deposition. Thus, any technical or non-technical technique may be used. Also the catalyst may take any of the forms discussed above (granular, tablets, etc.).

One method for making the catalysts of this invention is by mixing solutions or suspensions that include the metal precursors, driving off the solvent and converting at least part of the precursors into oxides. See also U.S. Pat. No. 4,250,346, incorporated herein by reference. The metal precursors comprise the desired metal in a solution or suspension in a desired amount in a suitable solvent. The metal precursor solution is prepared by dissolving a least part of a soluble compound of each of the metals or elements so as to provide the desired ratios of the metals or elements in the catalyst composition. One specific preferred metal precursor is a Ta precursor that is prepared by slowly hydrolyzing tantalum ethoxide in oxalic acid and water and then diluting making a tantalum oxalate. This process works particularly well for group 5 metals, such as Ta and Nb and is preferred because it provides a soluble Ta or Nb precursor, it is chloride free and generally provides better performance. Previous Ta solutions included chloride, which is not desirable generally. Details of specific metal precursors are disclosed in the examples. A metal precursor solution or suspension may be prepared for each metal or element in the desired catalyst composition, or a single metal precursor solution may include multiple metals or elements. After mixing the metal precursors, the solvent is driven off by any one a variety of techniques known to those of skill in the art, such as evaporation, freeze drying, etc. Thereafter, the composition is calcinated. Calcination is typically carried out at a temperature in the range of from about 200° C. to about 1000° C. Preferred calcination temperatures are less than 600° C. or less than 500° C. and greater than 250° C. or greater than 300° C. Calcination of the samples can be for ½ hour to 24 hours, more specifically from 1 to 12 hours and even more specifically from about 1 to 6 hours. Calcination may be carried out in an atmosphere of air. Preferably, there is a ramp up in the calcination temperature, as disclosed in the examples.

Choice of calcination conditions can affect the activity of the catalyst depending on the catalyst composition and dehydrogenation reaction conditions. For example, by lowering the calcination temperature, Ni—Nb—Ta oxides are generally more active for catalyzing ethane oxidative dehydrogenation at low temperature with higher conversions. As specifically shown in the examples, a calcination temperature for Ni—Nb—Ta oxides of about 400° C. gave generally lower conversions in comparison to a calcination temperature of about 300° C.

One preferred method is an aqueous method where various aqueous solutions comprised of water-soluble metal precursors are combined in proper volumetric ratios to obtain mixtures having desired metal compositions. Next, water is separated from the mixtures by lyophilization or precipitation. Lyophilization refers to freezing the resulting mixture under liquid nitrogen, and then placing the mixture in a high vacuum so that the water (ice) sublimes, leaving behind mixtures of dry metal precursors. Precipitation refers to separating dissolved metal ions by adding one or more chemical reagents that will precipitate sparingly soluble salts of the metal ions. Such chemical reagents may provide ions that shift ionic equilibria to favor formation of insoluble metal salts (common ion effect), or may bind with metal ions to form uncharged, insoluble coordination compounds (complexation). In addition, such reagents may oxidize or reduce metal ions to form ionic species that produce insoluble salts. Other precipitation mechanisms include hydrolysis, in which metal ions react with water in the presence of a weak base to form insoluble metal salts. Whatever the mechanism, the precipitate is separated from the remaining solution by first centrifuging the solutions and then decanting the supernatant; residual water can be removed by heating the precipitates or in vacuum. Finally, whether prepared by the sol-gel method or by the aqueous methods, the dry mixtures are calcined and may be ground to ensure a consistent bulk density among samples.

In addition, the usefulness of the catalysts of this invention is not necessarily limited to dehydrogenation reactions. Other useful reactions that may be performed with the catalysts include selective oxidation, ammoxidation, amination, homo and cross carbon-carbon coupling, dimerization and isomerization reactions.

EXAMPLES

The following examples are intended as illustrative and non-limiting, and represent specific embodiments of the present invention.

Example 1
Ni—Co—Nb Oxide Mixtures

Catalysts were prepared by an aqueous method. One molar nickel and 1.0 M cobalt stock solutions were prepared by dissolving 29.088 g of nickel (II) nitrate hexahydrate in distilled water to a final volume of 100 ml and by dissolving 29.129 g of cobalt (II) nitrate hexahydrate in distilled water to a final volume of 100 ml, respectively. A 1.0 M niobium stock solution was prepared by slowly hydrolyzing 100 mmol niobium ethoxide in an oxalic acid solution (2.7 M) in distilled water at 60° C. and diluted to 100 ml in volume after cooling to 25° C. A CAVRO automated liquid dispensing system was used to deliver aliquots of the aqueous stock solutions into 28 vessels. Each vessel contained 2250 µl of solution, and the molar concentrations of the metal ions in each vessel were given by expressions:

$$[Ni]_{i,j} = \frac{2000 - 300(i-1)}{2250}, M \quad \text{IV}$$

$$[Co]_{i,j} = \frac{200 + 300(j-1)}{2250}, M \quad \text{V}$$

$$[Nb]_{i,j} = \frac{50 + 75(i-j)}{2250}, M \quad \text{VI}$$

In expressions IV through VI, subscripts i and j represent row and column indices of a 7-by-7 triangular array, respectively, and $i \geq j$, i=1, ..., 7, and j=1, ..., 7.

Water was separated from the mixtures by lyophilization (freeze drying). Each of the 28 aqueous solutions were frozen under liquid nitrogen, and then placed in a high vacuum to vaporize the ice. The resulting dry mixtures were placed in an oven for calcination. The temperature of the oven was increased from room temperature to 120° C. at a rate of 1° C./min. The oven temperature was maintained at 120° C. for 2 hours, and was then ramped at 1° C./min. to 180° C. The oven temperature was held at 180° C. for 2 hours and was then ramped at 2° C./min. to 400° C. After 8 hours at 400° C., the oxide mixtures were removed from the oven and were allowed to cool to room temperature. The bulk samples were ground with a spatula to ensure consistent bulk density.

The catalyst compositions were each contacted with a gas mixture comprised of ethane and oxygen and by measuring the composition of the gas mixture following contact with the bulk samples. The best performing catalysts were those that yielded the highest ethane conversion and ethylene selectivity. Contacting was carried out in a 48-vessel parallel fixed bed reactor as described in U.S. patent application Ser. No. 09/093,870, "Parallel Fixed Bed Reactor and Fluid Contacting Apparatus and Method," filed Jun. 9, 1998, which is incorporated herein by reference.

Table 1 lists the composition and mass of Ni—Co—Nb oxide mixtures tested. High purity ethane and 14.4% $O_2$ in $N_2$ were obtained from MATHESON. Pure $N_2$ was obtained from an in-house supply line. After loading the reactor vessels with the 28 catalysts, the vessels were purged with $N_2$ to remove residual $O_2$. Next, the vessels were purged with ethane for another ten minutes. The composition of the effluent from each of the vessels was measured by gas chromatography (GC) to ensure that the ethane level had reached 95% prior to screening. The $O_2/N_2$ mixture was then added so that the reactant flow rate was 0.524 sccm per minute per reactor vessel, and the reactant gas composition was 40.1% $C_2H_6$, 8.4% $O_2$ and 51.5% $N_2$. Gas flow stability was measured periodically by GC. Two VARIAN 3800, 3-channel gas chromatographs were used to detect ethylene in vessel effluent. Each of the three channels contained 6-inch HAYESEP columns, methanizers, and flame-ionization detectors. CO, $CO_2$, $C_2H_4$, and $C_2H_6$ were separated to baseline in about three minutes. The responses of the flame ionization detectors and the methanizers were calibrated using a standard gas mixture containing 2.0% CO, 2.0% $CO_2$, 6.0% $C_2H_4$, 30.0% $C_2H_6$, 4.0% $O_2$ and the balance N experiments were carried out to generate calibration coefficients. Reactor (vessel) temperature was maintained at 300° C., and reactions were carried out at 15 psia. Tables 2 and 3 list ethane conversion and ethylene selectivity, respectively, for each of the Ni—Co—Nb oxide mixtures listed in Table 1.

Example 2
Ni—Co—Nb Oxide Mixtures

Table 4 lists composition and mass of Ni—Co—Nb oxides belonging to a second library. Like the bulk samples described in Example 1, the oxide mixtures shown in Table 4 were prepared from aqueous stock solutions of nickel (II) nitrate hexahydrate, cobalt (II) nitrate hexahydrate and niobium (V) oxalate. A CAVRO automated liquid dispensing system was used to deliver aliquots of the aqueous stock solutions into vessels. Water was separated from the mixtures by lyophilization, and the resulting dry mixtures were placed in an oven to oxidize the metal precursors in accordance with the temperature-time profile described in Example 1. The bulk samples were ground with a spatula to ensure consistent bulk density, and were evaluated for catalytic performance by contacting each sample with ethane and oxygen in a parallel fixed bed reactor. Reaction conditions were the same as those used to evaluate the mixed oxides shown in Table 1 of Example 1. Table 5 and 6 list ethane conversion and ethylene selectivity at 300° C., respectively, for each of the Ni—Co—Nb oxide mixtures listed in Table 4.

Example 3
Ni—Co—Nb Oxide Mixtures

Table 7 lists composition and mass of Ni—Co—Nb oxides belonging to a third library. Like the bulk samples described in Example 1, the oxide mixtures shown in Table 7 were prepared from aqueous stock solutions of nickel (II) nitrate hexahydrate, cobalt (II) nitrate hexahydrate and niobium (V) oxalate. A CAVRO automated liquid dispensing system was used to deliver aliquots of the aqueous stock solutions into vessels. Water was separated from the mixtures by lyophilization, and the resulting dry mixtures were placed in an oven to oxidize the metal precursors in accordance with the temperature-time profile described in Example 1. The bulk samples were ground with a spatula to ensure consistent bulk density, and were evaluated for catalytic performance in ODHE by contacting each sample with ethane and oxygen in a parallel fixed bed reactor. Reaction conditions were the same as those used to evaluate the mixed oxides shown in Table 1 of Example 1, except that the reactant flow rate was 1.048 sccm per minute per vessel. Table 8 and 9 list ethane conversion and ethylene selectivity at 300° C., respectively, for each of the Ni—Co—Nb oxide mixtures listed in Table 7.

Example 4
Ni—Co—Nb Oxide Mixtures 66 bulk samples of Ni—Co—Nb oxide mixtures were prepared and tested. The compositions of the oxide mixtures, which are listed in Table 10, encompassed a full range of ternary mixtures. Like the bulk samples described in Example 1, the oxide mixtures shown in Table 10 were prepared from aqueous stock solutions of nickel (II) nitrate hexahydrate, cobalt (II) nitrate hexahydrate and niobium (V) oxalate. A CAVRO automated liquid dispensing system was used to deliver aliquots of the aqueous stock solutions into vessels. The samples were lyophilized, calcined and ground in a manner similar to the mixed oxides shown in Table 1 of Example 1, and were evaluated for catalytic performance by contacting each sample with ethane and oxygen in a parallel fixed bed reactor. Reaction conditions were the same as those used to evaluate the mixed oxides shown in Table 7 of Example 3. Tables 11 and 12 list ethane conversion and ethylene selectivity at 300° C., respectively, for each of the Ni—Co—Nb oxide mixtures listed in Table 12.

Example 5
Ni—Co—Nb Oxide Mixtures

Table 13 lists composition and mass of Ni—Co—Nb oxides belonging to a fourth library. Like the bulk samples described in Example 1, the oxide mixtures shown in Table 13 were prepared from 1.0 M nickel (II) nitrate hexahydrate, 1.0 M cobalt (II) nitrate hexahydrate and 1.0 M niobium (V) oxalate aqueous stock solutions. A CAVRO automated liquid dispensing system was used to deliver aliquots of the aqueous stock solutions into vessels. Each vessel contained about 1.9 ml of solution. In contrast to Example 1, the metal precursors were separated from the aqueous phase by precipitation. One ml of ammonium hydroxide (28% ammonia in water) was added to each of the solutions resulting in a solid precipitate. The solid precipitate was separated from the aqueous phase by centrifuging at 4000 rpm for 20 minutes, followed by decanting the supernatant. The solid was dried in a vacuum oven at 60° C. for about an hour, and then calcined in accordance with the temperature-time profile described in Example 1. The bulk samples were ground with a spatula to ensure consistent bulk density, and were evaluated for catalytic performance in ODHE by contacting each sample with ethane and oxygen in a parallel fixed bed reactor. Reaction conditions were the same as those used to evaluate the mixed oxides shown in Table 7 of Example 3. Table 14 and 15 list ethane conversion and ethylene selectivity at 300° C., respectively, for each of the Ni—Co—Nb oxide mixtures listed in Table 13.

Example 6
Ni—Nb and Ni—Co—Nb Oxide Mixtures: Effect of Sample Mass, Reaction Temperature and Oxygen Content of Reactor Feed on Ethane Conversion and Selectivity; Comparison with Optimized Mo—V—Nb Oxide Catalyst FIG. 1 illustrates ethane conversion and ethylene selectivity as a function of reaction temperature for two of the catalysts in Table 13 of Example 5—$Ni_{0.63}Nb_{0.37}$ and $Ni_{0.55}Nb_{0.45}$—as well as an optimized Mo—V—Nb catalyst. The catalysts were evaluated in a parallel fixed bed reactor at temperatures ranging from 250° C. to 350° C. The Ni—Nb catalysts were tested at two different sample masses, while the Mo—V—Nb catalyst was tested at three different sample masses. Reactant flow rate was 1.048 sccm per minute per reactor vessel (sample), and the reactant gas was comprised of 40.1% $C_2H_6$, 8.4% $O_2$ and 51.5% $N_2$. Ethane conversion curves are shown for $Ni_{0.63}Nb_{0.37}$ (10.0 mg, 37.0 mg) 202, 204; $Ni_{0.55}Nb_{0.45}$ (16.4 mg, 48.9 mg) 206, 208; and Mo—V—Nb (12.3 mg, 23.4 mg, 72.2 mg) 210, 212, 214. Ethylene selectivity curves are shown for $Ni_{0.63}Nb_{0.37}$ (10.0 mg, 37.0 mg) 216, 218; $Ni_{0.55}Nb_{0.45}$ (16.4 mg, 48.9 ) 220, 222; and Mo—V—Nb (12.3 mg, 23.4 mg, 72.2 mg) 224, 226, 228.

Figure 2:
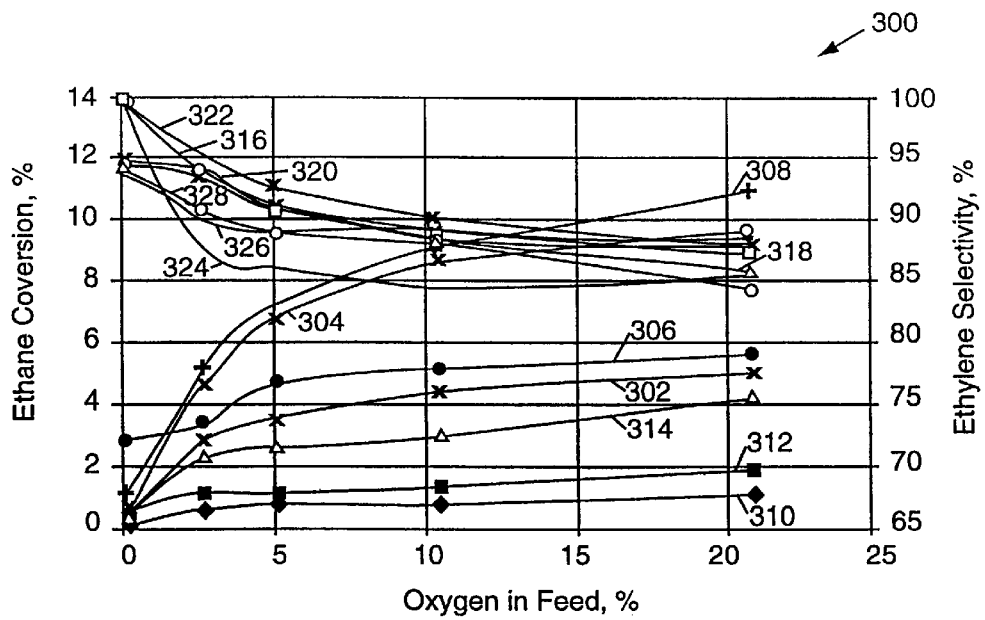
FIG. 2 shows ethane conversion and ethylene selectivity as a function of oxygen content of reactor feed for Ni—Nb oxide mixtures and for an optimized Mo—V—Nb catalyst.

FIG. 2 illustrates ethane conversion and ethylene selectivity as a function of oxygen content of the reactor feed for the two Ni—Nb catalysts and the optimized Mo—V—Nb catalyst. The catalysts were evaluated in the parallel fixed bed reactor at 300° C. As in FIG. 2, the Ni—Nb catalysts were tested at two different sample masses, and the Mo—V—Nb catalyst was tested at three different sample masses. In all cases, reactant flow rate was 1.048 sccm per minute per reactor vessel (sample). The reactant feed was comprised of 0% to 21% $O_2$, 51.5% $N_2$, and the balance $C_2H_6$. Ethane conversion curves are shown for $Ni_{0.63}Nb_{0.37}$ (10.0 mg, 37.0 mg) 302, 304; $Ni_{0.55}Nb_{0.45}$ (16.4 mg, 48.9 mg) 306, 308; and Mo—V—Nb (12.3 mg, 23.4 mg, 72.2 mg) 310, 312, 314. Ethylene selectivity curves are shown for $Ni_{0.63}Nb_{0.37}$ (10.0 mg, 37.0 mg) 316, 318; $Ni_{0.55}Nb_{0.45}$ (16.4 mg, 48.9 mg) 320, 322; and Mo—V—Nb (12.3 mg, 23.4 mg, 72.2 mg) 324,326 328.

Figure 3:
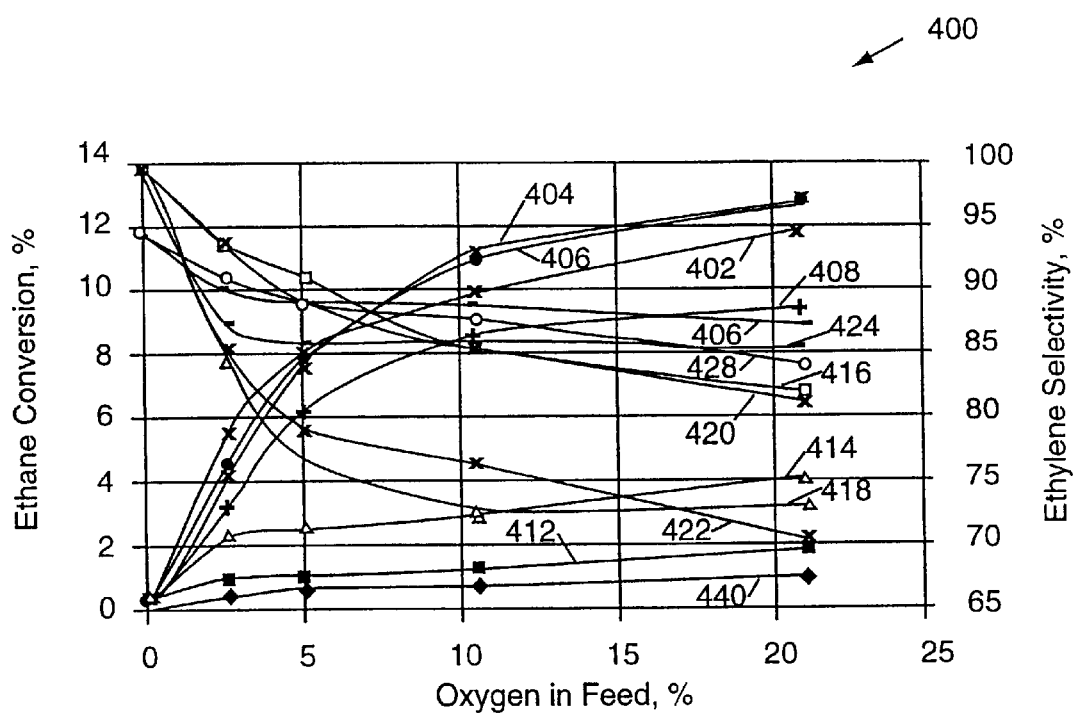
FIG. 3 shows ethane conversion and ethylene selectivity as a function of oxygen content of reactor feed for Ni—Co—Nb oxide mixtures and for an optimized Mo—V—Nb catalyst.

FIG. 3 illustrates ethane conversion and ethylene selectivity as a function of the amount of oxygen in the reactor feed for four catalysts shown in Table 13 that contain small amounts of cobalt—$Ni_{0.81}Co_{0.04}Nb_{0.16}$, $Ni_{0.65}Co_{0.04}Nb_{0.31}$, $Ni_{0.58}Co_{0.04}Nb_{0.39}$ and $Ni_{0.60}Co_{0.08}Nb_{0.32}$. For comparison, FIG. 3 also shows ethane conversion and ethylene selectivity for the optimized Mo—V—Nb catalyst. The catalysts were evaluated in the parallel fixed bed reactor at 300° C. The Ni—Co—Nb catalysts were each tested at one sample mass, and the Mo—V—Nb catalyst was tested at three different sample masses. In all cases, reactant flow rate was 1.048 sccm per minute per reactor vessel (sample). The reactant feed was comprised of 0% to 21% $O_2$, 51.5% $N_2$, and the balance $C_2H_6$. Ethane conversion curves are shown for $Ni_{0.81}Co_{0.04}Nb_{0.16}$ (35.8 mg) 402; $Ni_{0.65}Co_{0.04}Nb_{0.31}$ (32.4 mg) 404; $Ni_{0.58}Co_{0.04}Nb_{0.39}$ (38.3 mg) 406; $Ni_{0.60}Co_{0.08}Nb_{0.32}$ (30.2 mg) 408; and Mo—V—Nb (12.3 mg, 23.4 mg, 72.2 mg) 410, 412, 414. Ethylene selectivity curves are shown for $Ni_{0.81}Co_{0.04}Nb_{0.16}$ (35.8 mg) 416; $Ni_{0.65}Co_{0.04}Nb_{0.31}$ (32.4 mg) 418; $Ni_{0.58}Co_{0.04}Nb_{0.39}$ (38.3 mg) 420; $Ni_{0.60}Co_{0.08}Nb_{0.32}$ (30.2 mg) 422; and Mo—V—Nb (12.3 mg, 23.4 mg, 72.2 mg) 424, 426, 428.

Example 7
Ni—Nb—Ta—K Oxide Mixtures

Table 16 lists composition and mass of a focused Ni—Nb—Ta—K oxide library. The oxide mixtures were selected based on the primary screening results shown in Table 21 and were prepared from 1.0 M nickel (II) nitrate hexahydrate, 0.70 M niobium (V) oxalate, 0.87 M tantalum oxalate and 1.07 M potassium nitrate aqueous stock solutions. A CAVRO automated liquid dispensing system was used to deliver aliquots of the aqueous stock solutions into vessels. Water was separated from the mixtures by lyophilization, and the resulting dry mixtures were placed in an oven to oxidize the metal precursors in accordance with the temperature-time profile described in Example 1. The bulk samples were ground with a spatula to ensure consistent bulk density, and were evaluated for catalytic performance in ODHE by contacting each sample with ethane and oxygen in the parallel fixed bed reactor. Reactant flow rate was 1.048 sccm per minute per reactor vessel (sample), and the reactant gas was comprised of 40.1% $C_2H_6$, 8.4% $O_2$ and 51.5% $N_2$. Tables 17 and 18 list ethane conversion and ethylene selectivity at 300° C., respectively, for each of the Ni—Nb—Ta—K oxide mixtures listed in Table 16.

Example 8
Ni—Nb—Ta Oxide Mixtures

Table 19 lists composition and mass of a Ni—Nb—Ta oxide library. Bulk samples of the oxide mixtures shown in Table 19 were prepared from 1.0 M nickel (II) nitrate hexahydrate, 1.0 M niobium (V) oxalate and 1.0 M tantalum oxalate aqueous stock solutions. A CAVRO automated liquid dispensing system was used to deliver aliquots of the aqueous stock solutions into vessels. Each vessel contained about 1.9 ml of solution. Like Example 5, the metal precursors were separated from the aqueous phase by precipitation. One ml of ammonium hydroxide (28% ammonia in water) was added to each of the solutions resulting in a solid precipitate. The solid precipitate was separated from the aqueous phase by centrifuging at 4000 rpm for 20 minutes, followed by decanting the supernatant. The solid was dried in a vacuum oven at 60° C. for about an hour, and then calcined in accordance with the temperature-time profile described in Example 1. The bulk samples were ground with a spatula to ensure consistent bulk density, and were evaluated for catalytic performance in ODHE by contacting each sample with ethane and oxygen in a parallel fixed bed reactor. Reactant flow rate was 1.048 sccm per minute per reactor vessel (sample), and the reactant gas was comprised of 40.1% $C_2H_6$, 8.4% $O_2$ and 51.5% $N_2$. Tables 20 and 21 list ethane conversion and ethylene selectivity at 300° C., respectively, for each of the Ni—Nb—Ta oxide mixtures listed in Table 19.

Example 9
Ni—Nb—Ta Oxide Mixtures: Ethylene in Reactor Feed

Table 22 lists composition and mass of a Ni—Nb-Ta oxide library. The oxide mixtures shown in Table 22 were prepared from 1.0 M nickel (II) nitrate hexahydrate, 1.0 M niobium (V) oxalate and 1.0 M tantalum oxalate aqueous stock solutions, as disclosed above. A CAVRO automated liquid dispensing system was used to deliver aliquots of the aqueous stock solutions into vessels. Each vessel contained about 3.3 ml of solution. The metal precursors were from the aqueous phase by precipitation. About 2.9 ml of a 1.57 M ammonium carbonate solution was added to each of the solutions resulting in a solid precipitate. The solid precipitate was separated from the aqueous phase by centrifuging at 4000 rpm for 20 minutes, followed by decanting the supernatant. The solid was dried in a vacuum oven at 60° C. for about an hour, and then calcined in accordance with the temperature-time profile described in Example 1. The bulk samples were ground with a spatula to ensure consistent bulk density, and were evaluated for catalytic performance in ODHE by contacting each sample with ethane and oxygen in a parallel fixed bed reactor. Reactant flow rate was 1.048 sccm per minute per reactor vessel (sample), and the reactant gas was comprised of 40.1% $C_2H_6$, 8.4% $O_2$ and 51.5% $N_2$. Table 23 and 24 ethane conversion and ethylene selectivity at 300° C., respectively, for each of the Ni—Nb—Ta oxide mixtures listed in Table 22. Table 25 and 26 list ethane conversion and ethylene selectivity at 325° C.

To determine the effect of ethylene in the reactor feed on ethane conversion and ethylene selectivity, the mixed oxide samples listed in Table 22 were contacted with a gas mixture comprised of 11.2% $C_2H_4$, 28.1% $C_2H_6$, 0.8% $CO_2$, 8.4% $O_2$ and 51.5% $N_2$. Reactant flow rate was maintained at 1.048 sccm per minute per reactor vessel (sample), and the fractions of $C_2H_4$, $C_2H_6$ and $CO_2$ in the reactor feed were verified during screening by measuring the composition of gas effluent from blank vessels in the parallel fixed bed reactor. Tables 27 and 28, which list changes in ethane and ethylene concentration following contact with the Ni—Nb—Ta oxide mixtures, show significant ethane conversion to ethylene at 325° C. Table 29 lists CO and $CO_2$ production at 325° C.

Example 10
Ni—Nb—Ta Oxide Mixtures: Ethylene in Reactor Feed

Table 30 lists composition and mass of another Ni—Nb—Ta oxide library. The oxide mixtures shown in Table 30 were prepared from 1.0 M nickel (II) nitrate hexahydrate, 1.0 M niobium (V) oxalate and 1.0 M tantalum oxalate aqueous stock solutions. A CAVRO automated liquid dispensing system was used to deliver aliquots of the aqueous stock solutions into vessels. Each vessel contained about 3.3 ml of solution. The metal precursors were separated from the aqueous phase by precipitation. About 2.9 ml of a 1.57 M ammonium carbonate solution was added to each of the solutions resulting in a solid precipitate. The solid precipitate was separated from the aqueous phase by centrifuging at 4000 rpm for 20 minutes, followed by decanting the supernatant. The solid was dried in a vacuum oven at 60° C. for about an hour, and then calcined in accordance with the temperature-time profile described in Example 1. The bulk samples were ground with a spatula to ensure consistent bulk density, and were evaluated for catalytic performance in ODHE by contacting each sample with ethane and oxygen in a parallel fixed bed reactor. Reactant flow rate was 1.048 sccm per minute per reactor vessel (sample), and the reactant gas was comprised of 40.1% $C_2H_6$, 8.4% $O_2$ and 51.5% $N_2$. Table 31 and 32 list ethane conversion and ethylene selectivity at 300° C., respectively, for each of the Ni—Nb—Ta oxide mixtures listed in Table 30. Table 33 and 34 list ethane conversion and ethylene selectivity at 325° C.

To determine the effect of ethylene in the reactor feed on ethane conversion and ethylene selectivity, the mixed oxide samples listed in Table 30 were contacted with a gas mixture comprised of 11.2% $C_2H_4$, 28.5% $C_2H_6$, 8.4% $O_2$ and 51.5% $N_2$. Reactant flow maintained at 1.048 sccm per minute per reactor vessel (sample), and the fractions of $C_2H_4$, $C_2H_6$ and $CO_2$ in the reactor feed were verified during screening by measuring the composition of gas effluent from blank vessels in the parallel fixed bed reactor. Tables 35 and 36, which list changes in ethane and ethylene concentration following contact with the Ni—Nb—Ta oxide mixtures, show significant ethane conversion to ethylene at 325° C. Table 37 lists CO and $CO_2$ production at 325° C.

Example 11

Ni—Nb—a Oxide Mixtures at Lower Calcination Temperature

Table 38 lists composition and mass of a Ni—Nb—Ta oxide library. Bulk samples of the oxide mixtures shown in Table 38 were prepared from 1.0 M nickel (II) nitrate hexahydrate, 1.0 M niobium (V) oxalate and 1.0 M tantalum oxalate aqueous stock solutions. A CAVRO automated liquid dispensing system was used to deliver aliquots of the aqueous stock solutions into vessels. Each vessel contained about 1.9 ml of solution. Like Example 5, the metal precursors were separated from the aqueous phase by precipitation. Ammonium carbonate (1.62 M) was added to each of the solutions resulting in a solid precipitate. The mixture was allowed to settle at 25° C. for 3 hours. The solid precipitate was separated from the aqueous phase by centrifuging at 4000 rpm for 10 minutes, followed by decanting the supernatant. The solid was dried in a vacuum oven at 60° C. for about an hour. The solid obtained was calcined in air under the following temperature-time profile: The temperature of the oven was increased from room temperature to 300° C. at a rate of 2° C./min. The oven temperature was held at 300° C. for 8 hours. After 8 hours at 300° C., the oxide mixtures were removed from the oven and were allowed to cool to room temperature. The bulk samples were ground with a spatula to ensure consistent bulk density. The bulk samples were evaluated for catalytic performance by contacting each sample with ethane and oxygen in a parallel fixed bed reactor, described in Example 1. Reactant flow rate was 1.048 sccm per minute per reactor vessel (sample), and the reactant gas was comprised of 40.1% $C_2H_6$, 8.4% $O_2$ and 51.5% $N_2$. Tables 39 and 40 list ethane conversion and ethylene selectivity at 300° C., respectively, for each of the Ni—Nb—Ta oxide mixtures listed in Table 38. The ethane dehydrogenation reaction was also carried out at 250° C. and Tables 41 and 42 list ethane conversion and ethylene selectivity at 250° C., respectively, for each of the Ni—Nb—Ta oxide mixtures listed in Table 38.

To determine the effect of ethylene in the reactor feed on ethane conversion and ethylene selectivity, selected mixed oxide samples listed in Table 38 were contacted in the parallel fixed bed reaction with a gas mixture comprised of 11.3% $C_2H_4$, 28.7% $C_2H_6$, 8.4% $O_2$ and 51.5% $N_2$. Reactant flow rate was maintained at 1.048 sccm per minute per reactor vessel (sample), and the fractions of $C_2H_4$, $C_2H_6$ and $CO_2$ in the reactor feed were verified during screening by measuring the composition of gas effluent from blank vessels in the parallel fixed bed reactor. Tables 43 and 44, which list the selected samples as well as changes in ethane and ethylene concentration following contact with the Ni—Nb—Ta oxide mixtures, show significant ethane conversion to ethylene at 300° C. Table 45 lists $CO_2$ production at 300° C. The test was repeated at 275° C. for the same selected samples.

Example 12

Ni—Nb, Ni—Co, Ni—Co—Nb, Ni—Nb—Al, Ni—Nb—Fe and Optimized Mo—V—Nb Oxide Mixtures: Ethylene in Reactor Feed Table 46 lists composition and mass of Ni—Nb, Ni—Co, Ni—Co—Nb, Ni—Nb—Al and Ni—Nb—Fe oxide mixtures, as well as an optimized Mo—V—Nb oxide catalyst. Bulk samples of each of these oxide mixtures were prepared using aqueous methods described above. For the Ni—Nb—Al and Ni—Nb—Fe oxide mixtures, methods similar to those of Example 5 were followed except that 1.0M aluminum nitrate and 1.0M ferric nitrate, were used, respectively. Bulk samples were evaluated for catalytic performance in ODHE by contacting each sample with ethane, ethylene and oxygen in the parallel fixed bed reactor. The reactant gas was comprised of 11.6% $C_2H_4$, 28.5% $C_2H_6$, 8.4% $O_2$ and 51.5% $N_2$. Reactant flow rate was maintained at 1.048 sccm per minute per reactor vessel (sample), and fractions of $C_2H_4$ and $C_2H_6$ in the reactor feed were verified during screening by measuring the composition of gas effluent from blank vessels in the parallel fixed bed reactor. Table 46, which also lists changes in ethane and ethylene concentration following contact with the oxide mixtures, shows significant ethane conversion to ethylene for many of the mixed oxides. Notable exceptions include two of the Mo—V—Nb oxide samples.

Example 13

Ni—Nb Oxide Mixtures: Effect of Preparation on Performance

To gauge the influence of the bulk sample preparation method on catalyst performance, Ni—Nb oxide compositions were prepared using six different reagents to precipitate the metal precursors. The reagents include ammonium hydroxide, tetraethylammonium hydroxide, potassium carbonate, sodium hydroxide, potassium hydroxide, and ammonium carbonate, as follows: Ammonium hydroxide: 1.0 ml of ammonium hydroxide (28% ammonia in water) was added to a solution of nickel nitrate (1.0M, 1.29 ml), niobium oxalate (1.07M, 0.57 ml), and Cobalt (II) nitrate (0.07 ml, 1.0M). The resulting mixture was centrifuged at 4000 rpm for 20 minutes and the solution was decanted. The solid was dried in a vacuum oven at 60° C. and then calcined at a maximum temperature of 400° C. Ammonium carbonate: 2.9 ml of ammonium carbonate (1.57M) was added to a solution of nickel nitrate (1.0M, 1.53 ml), niobium oxalate (0.52M, 0.87 ml), and Tantalum oxalate (0.87 ml, 0.52M). Foam ($CO_2$) was formed accompanied with the formation of a solid. The resulting mixture was centrifuged at 4000 rpm for 20 minutes and the solution was decanted. To the solid, about 5 ml of distilled water was added and then mixed. The resulting mixture was centrifuged at 4000 rpm for 20 minutes and the solution was decanted. The solid was dried in a vacuum oven at 60° C. and then calcined at a maximum temperature of 400° C. Tetraethylammonium hydroxide: 4.4 ml of tetraethylamminium hydroxide (1.14M) was added to a solution of nickel nitrate (1.0M, 2.60 ml) and niobium oxalate (0.70M, 0.70 ml). The resulting mixture was centrifuged at 4000 rpm for 20 minutes and the solution was decanted. To the solid, about 5 ml of distilled water was added and then mixed. The resulting mixture was centrifuged at 4000 rpm for 20 minutes and the solution was decanted. The solid was dried in a vacuum oven at 60° C. and then calcined at a maximum temperature of 400° C. Potassium hydroxide: 0.6 ml of potassium hydroxide (5.26M in water) was added to a solution of nickel nitrate (1.0M, 1.50 ml) and niobium oxalate (0.70M, 0.30 ml). The resulting mixture was centrifuged at 4000 rpm for 20 minutes and the solution was decanted. To the solid, about 5 ml of distilled water was added and then mixed. The resulting mixture was centrifuged at 4000 rpm for 20 minutes and the solution was decanted. The solid was dried in a vacuum oven at 60° C. and then calcined at a maximum temperature of 400° C. Sodium hydroxide: 1.0 ml of sodium hydroxide (3.0M in water) was added to a solution of nickel nitrate (1.0M, 1.50 ml) and niobium oxalate (0.7M, 0.30 ml). The resulting mixture was centrifuged at 4000 rpm for 20 minutes and the solution was decanted. To the solid, about 5 ml of distilled water was added and then mixed. The resulting mixture was centrifuged at 4000 rpm for 20 minutes and the solution was decanted. The solid was dried in a vacuum oven at 60° C. and then calcined at a maximum temperature of 400° C. Potassium carbonate: 1.5 ml of potassium carbonate (2.04M in water) was added to a solution of nickel nitrate (1.0M, 1.50 ml) and niobium oxalate (0.70M, 0.30 ml). The resulting mixture was centrifuged at 4000 rpm for 20 minutes and the solution was decanted. To the solid, about 5 ml of distilled water was added and then mixed. The resulting mixture was centrifuged at 4000 rpm for 20 minutes and the solution was decanted. The solid was dried in a vacuum oven at 60° C. and then calcined at a maximum temperature of 400° C. Table 47 lists the compositions of the Ni—Nb oxide mixtures, which were evaluated for catalytic performance in ODHE by contacting each sample with ethane and oxygen in a parallel fixed bed reactor. Reactant flow rate was 1.048 sccm per minute per reactor vessel (sample), and the reactant gas was comprised of 40.1% $C_2H_6$, 8.4% $O_2$ and 51.5% $N_2$. Tables 48 and 49 list ethane conversion and ethylene selectivity at 300° C., respectively, for each of the Ni—Nb oxide mixtures prepared using the six different reagents.

Example 14

Ni—Ta Oxide Mixtures

Table 50 lists composition and mass of a Ni—Ta oxide library. The oxide mixtures were prepared from 1.0 M nickel (II) nitrate hexahydrate and 1.0 M tantalum oxalate aqueous stock solutions. A CAVRO automated liquid dispensing system was used to deliver aliquots of the aqueous stock solutions into vessels. Each vessel contained about 3.3 ml of solution. About 1.1 ml of a 1.14 M tetraethylammonium hydroxide solution was added to each of the solutions resulting in a solid precipitate. The solid precipitate was separated from the aqueous phase by centrifuging at 4000 rpm for 20 minutes, followed by decanting the supernatant. The solid was dried in a vacuum oven at 60° C. for about an hour, and then calcined in accordance with the temperature-time profile described in Example 1. The bulk samples were ground with a spatula to ensure consistent bulk density, and were evaluated for catalytic performance in ODHE by contacting each sample with ethane and oxygen in a parallel fixed bed reactor. Reactant flow rate was 1.048 sccm per minute per reactor vessel (sample), and the reactant gas was comprised of 40.1% $C_2H_6$, 8.4% $O_2$ and 51.5% $N_2$. Table 50 lists ethane conversion and ethylene selectivity at 300° C. for each of the Ni—Ta oxide mixtures.

It is to be understood that the above description is intended to be illustrative and not restrictive. Many embodiments will be apparent to those of skill in the art upon reading the above description. The scope of the invention should therefore be determined not with reference to the above description, but should instead be determined with reference to the appended claims, along with the full scope of equivalents to which such claims are entitled. The disclosures of all articles and references, including patent applications and publications, are incorporated herein by reference for all purposes.

TABLE 1

Composition and mass of Ni—Co—Nb oxide mixtures

| | | 1 | 2 | 3 | 4 | 5 | 6 | 7 |
|---|---|---|---|---|---|---|---|---|
| | | Mole Fraction & Sample Mass, mg | | | | | | |
| 1 | Ni | 0.89 | | | | | | |
| | Co | 0.09 | | | | | | |
| | Nb | 0.02 | | | | | | |
| | M | 59.3 | | | | | | |
| 2 | Ni | 0.84 | 0.76 | | | | | |
| | Co | 0.10 | 0.22 | | | | | |
| | Nb | 0.06 | 0.02 | | | | | |
| | M | 35.5 | 59.5 | | | | | |
| 3 | Ni | 0.78 | 0.69 | 0.62 | | | | |
| | Co | 0.11 | 0.25 | 0.36 | | | | |
| | Nb | 0.11 | 0.06 | 0.02 | | | | |
| | M | 31.4 | 39.7 | 49.4 | | | | |
| 4 | Ni | 0.70 | 0.61 | 0.54 | 0.49 | | | |
| | Co | 0.13 | 0.28 | 0.40 | 0.49 | | | |
| | Nb | 0.17 | 0.11 | 0.06 | 0.02 | | | |
| | M | 50.5 | 43.3 | 36.0 | 52.4 | | | |
| 5 | Ni | 0.59 | 0.51 | 0.44 | 0.40 | 0.36 | | |
| | Co | 0.15 | 0.32 | 0.44 | 0.54 | 0.62 | | |
| | Nb | 0.26 | 0.17 | 0.11 | 0.06 | 0.02 | | |
| | M | 46.9 | 48.6 | 33.8 | 52.3 | 48.9 | | |
| 6 | Ni | 0.44 | 0.37 | 0.32 | 0.28 | 0.25 | 0.22 | |
| | Co | 0.18 | 0.37 | 0.51 | 0.61 | 0.69 | 0.76 | |
| | Nb | 0.38 | 0.26 | 0.17 | 0.11 | 0.06 | 0.02 | |
| | M | 43.9 | 46.7 | 46.7 | 36.1 | 42.1 | 62.9 | |
| 7 | Ni | 0.22 | 0.18 | 0.15 | 0.13 | 0.11 | 0.10 | 0.09 |
| | Co | 0.22 | 0.44 | 0.59 | 0.70 | 0.78 | 0.84 | 0.89 |
| | Nb | 0.56 | 0.38 | 0.26 | 0.17 | 0.11 | 0.06 | 0.02 |
| | M | 45.8 | 46.8 | 47.3 | 50.7 | 45.7 | 65.4 | 48.5 |

TABLE 2

Ethane conversion of Ni—Co—Nb oxide mixtures listed in Table 1

| | 1 | 2 | 3 | 4 | 5 | 6 | 7 |
|---|---|---|---|---|---|---|---|
| | Ethane Conversion, % | | | | | | |
| 1 | 17.6 | | | | | | |
| 2 | 16.3 | 10.4 | | | | | |
| 3 | 15.0 | 10.1 | 11.8 | | | | |
| 4 | 17.1 | 10.9 | 11.2 | 10.0 | | | |
| 5 | 11.5 | 12.4 | 11.7 | 10.4 | 11.2 | | |
| 6 | 12.3 | 11.5 | 13.3 | 10.9 | 11.7 | 12.6 | |
| 7 | 9.6 | 11.5 | 9.3 | 12.4 | 11.7 | 11.8 | 10.9 |

TABLE 3

Ethylene selectivity of Ni—Co—Nb oxide mixtures listed in Table 1

| | 1 | 2 | 3 | 4 | 5 | 6 | 7 |
|---|---|---|---|---|---|---|---|
| | Ethylene Selectivity, % | | | | | | |
| 1 | 40.7 | | | | | | |
| 2 | 39.4 | 45.6 | | | | | |
| 3 | 46.8 | 42.1 | 31.6 | | | | |
| 4 | 61.3 | 48.5 | 29.8 | 31.9 | | | |
| 5 | 48.0 | 34.0 | 34.0 | 35.5 | 30.9 | | |
| 6 | 36.7 | 29.8 | 32.3 | 36.3 | 33.9 | 35.2 | |
| 7 | 30.6 | 30.5 | 38.9 | 35.3 | 32.6 | 33.2 | 37.4 |

TABLE 4

Composition and mass of Ni—Co—Nb oxide mixtures

| | | 1 | 2 | 3 | 4 | 5 | 6 |
|---|---|---|---|---|---|---|---|
| | | Mole Fraction & Sample Mass, mg | | | | | |
| 1 | Ni | 0.73 | 0.71 | 0.69 | 0.67 | 0.65 | 0.63 |
| | Co | 0.03 | 0.06 | 0.09 | 0.12 | 0.15 | 0.17 |
| | Nb | 0.23 | 0.23 | 0.22 | 0.21 | 0.21 | 0.20 |
| | M | 43.7 | 45.8 | 47.2 | 45.8 | 44.0 | 50.1 |

TABLE 4-continued

Composition and mass of Ni—Co—Nb oxide mixtures

| | | 1 | 2 | 3 | 4 | 5 | 6 |
|---|---|---|---|---|---|---|---|
| | | | | Mole Fraction & Sample Mass, mg | | | |
| 2 | Ni | 0.76 | 0.73 | 0.71 | 0.60 | 0.67 | 0.65 |
|   | Co | 0.03 | 0.07 | 0.10 | 0.13 | 0.15 | 0.18 |
|   | Nb | 0.21 | 0.20 | 0.19 | 0.19 | 0.18 | 0.18 |
|   | M  | 44.3 | 44.0 | 48.5 | 42.9 | 43.6 | 47.1 |
| 3 | Ni | 0.79 | 0.76 | 0.73 | 0.71 | 0.69 | 0.67 |
|   | Co | 0.04 | 0.07 | 0.10 | 0.13 | 0.16 | 0.18 |
|   | Nb | 0.18 | 0.17 | 0.17 | 0.16 | 0.16 | 0.15 |
|   | M  | 43.1 | 44.7 | 47.7 | 46.0 | 50.4 | 46.9 |
| 4 | Ni | 0.81 | 0.79 | 0.76 | 0.73 | 0.71 | 0.69 |
|   | Co | 0.04 | 0.07 | 0.10 | 0.13 | 0.16 | 0.19 |
|   | Nb | 0.14 | 0.14 | 0.14 | 0.13 | 0.13 | 0.13 |
|   | M  | 42.8 | 41.4 | 44.6 | 42.8 | 44.5 | 43.1 |

TABLE 5

Ethane conversion of Ni—Co—Nb oxide mixtures listed in Table 4

| | 1 | 2 | 3 | 4 | 5 | 6 |
|---|---|---|---|---|---|---|
| | | | Ethane Conversion, % | | | |
| 1 | 22.8 | 16.4 | 16.8 | 13.6 | 13.3 | 13.5 |
| 2 | 21.4 | 16.2 | 19.5 | 15.9 | 14.6 | 14.9 |
| 3 | 22.7 | 15.7 | 16.9 | 15.4 | 15.5 | 15.0 |
| 4 | 17.3 | 14.0 | 15.6 | 14.5 | 13.9 | 15.0 |

TABLE 6

Ethylene selectivity of Ni—Co—Nb oxide mixtures listed in Table 4

| | 1 | 2 | 3 | 4 | 5 | 6 |
|---|---|---|---|---|---|---|
| | | | Ethane Selectivity, % | | | |
| 1 | 62.2 | 70.1 | 56.4 | 52.7 | 45.8 | 44.0 |
| 2 | 66.3 | 69.8 | 66.1 | 61.5 | 50.1 | 46.3 |
| 3 | 64.8 | 71.7 | 61.8 | 60.8 | 55.7 | 52.3 |
| 4 | 63.8 | 69.6 | 59.8 | 57.0 | 51.3 | 48.0 |

TABLE 7

Composition and mass of Ni—Co—Nb oxide mixtures

| | | 1 | 2 | 3 | 4 |
|---|---|---|---|---|---|
| | | | Mole Fraction & Sample Mass, mg | | |
| 1 | Ni | 1.00 | | | |
|   | Co | 0.00 | | | |
|   | Nb | 0.00 | | | |
|   | M  | 45.6 | | | |
| 2 | Ni | 0.85 | 0.84 | 0.83 | 0.82 |
|   | Co | 0.00 | 0.01 | 0.02 | 0.03 |
|   | Nb | 0.15 | 0.15 | 0.15 | 0.15 |
|   | M  | 40.5 | 40.3 | 40.1 | 41.0 |
| 3 | Ni | 0.81 | 0.81 | 0.80 | 0.79 |
|   | Co | 0.00 | 0.01 | 0.02 | 0.03 |
|   | Nb | 0.19 | 0.18 | 0.18 | 0.18 |
|   | M  | 39.2 | 43.8 | 41.6 | 41.6 |
| 4 | Ni | 0.79 | 0.78 | 0.77 | 0.77 |
|   | Co | 0.00 | 0.01 | 0.02 | 0.03 |
|   | Nb | 0.21 | 0.21 | 0.21 | 0.21 |
|   | M  | 40.1 | 40.0 | 39.2 | 42.7 |
| 5 | Ni | 0.76 | 0.75 | 0.75 | 0.74 |
|   | Co | 0.00 | 0.01 | 0.02 | 0.03 |
|   | Nb | 0.24 | 0.24 | 0.24 | 0.24 |
|   | M  | 39.3 | 40.9 | 40.9 | 39.9 |
| 6 | Ni | 0.73 | 0.73 | 0.72 | 0.72 |
|   | Co | 0.00 | 0.01 | 0.02 | 0.02 |
|   | Nb | 0.27 | 0.26 | 0.26 | 0.26 |
|   | M  | 42.7 | 40.3 | 41.6 | 40.3 |
| 7 | Ni | 0.71 | 0.70 | 0.70 | 0.69 |
|   | Co | 0.00 | 0.01 | 0.02 | 0.02 |
|   | Nb | 0.29 | 0.29 | 0.29 | 0.28 |
|   | M  | 42.0 | 41.7 | 43.6 | 46.3 |
| 8 | Ni | 0.69 | | | |
|   | Co | 0.00 | | | |
|   | Nb | 0.31 | | | |
|   | M  | 42.8 | | | |
| 9 | Ni | 0.67 | | | |
|   | Co | 0.00 | | | |
|   | Nb | 0.33 | | | |
|   | M  | 41.3 | | | |
| 10 | Ni | 0.65 | | | |
|    | Co | 0.00 | | | |
|    | Nb | 0.35 | | | |
|    | M  | 41.4 | | | |
| 11 | Ni | 0.63 | | | |
|    | Co | 0.00 | | | |
|    | Nb | 0.37 | | | |
|    | M  | 40.9 | | | |
| 12 | Ni | 0.61 | | | |
|    | Co | 0.00 | | | |
|    | Nb | 0.39 | | | |
|    | M  | 40.0 | | | |
| 13 | Ni | 0.59 | | | |
|    | Co | 0.00 | | | |
|    | Nb | 0.41 | | | |
|    | M  | 41.8 | | | |
| 14 | Ni | 0.58 | | | |
|    | Co | 0.00 | | | |
|    | Nb | 0.42 | | | |
|    | M  | 40.9 | | | |
| 15 | Ni | 0.56 | | | |
|    | Co | 0.00 | | | |
|    | Nb | 0.44 | | | |
|    | M  | 41.2 | | | |
| 16 | Ni | 0.55 | | | |
|    | Co | 0.00 | | | |
|    | Nb | 0.45 | | | |
|    | M  | 41.8 | | | |
| 17 | Ni | 0.54 | | | |
|    | Co | 0.00 | | | |
|    | Nb | 0.46 | | | |
|    | M  | 40.0 | | | |
| 18 | Ni | 0.52 | | | |
|    | Co | 0.00 | | | |
|    | Nb | 0.48 | | | |
|    | M  | 40.8 | | | |
| 19 | Ni | 0.50 | | | |
|    | Co | 0.00 | | | |
|    | Nb | 0.50 | | | |
|    | M  | 41.5 | | | |

TABLE 8

Ethane conversion of Ni—Co—Nb oxide mixtures listed in Table 7

| | 1 | 2 | 3 | 4 |
|---|---|---|---|---|
| | | Ethane Conversion, % | | |
| 1 | 3.9  |      |      |      |
| 2 | 8.3  | 7.8  | 7.8  | 7.6  |
| 3 | 10.0 | 9.7  | 9.6  | 10.7 |
| 4 | 10.0 | 11.9 | 9.8  | 11.3 |
| 5 | 10.9 | 11.2 | 10.4 | 11.4 |
| 6 | 9.7  | 10.9 | 9.4  | 11.0 |
| 7 | 8.7  | 10.0 | 9.6  | 11.0 |

TABLE 8-continued

Ethane conversion of Ni—Co—Nb oxide mixtures listed in Table 7

| | 1 | 2 | 3 | 4 |
|---|---|---|---|---|
| | | Ethane Conversion, % | | |
| 8 | 9.8 | | | |
| 9 | 8.1 | | | |
| 10 | 7.2 | | | |
| 11 | 6.5 | | | |
| 12 | 5.7 | | | |
| 13 | 5.9 | | | |
| 14 | 5.5 | | | |
| 15 | 5.5 | | | |
| 16 | 4.3 | | | |
| 17 | 4.5 | | | |
| 18 | 4.4 | | | |
| 19 | 3.2 | | | |

TABLE 9

Ethylene selectivity of Ni—Co—Nb oxide mixtures listed in Table 7

| | 1 | 2 | 3 | 4 |
|---|---|---|---|---|
| | | Ethylene Selectivity, % | | |
| 1 | 16.2 | | | |
| 2 | 69.0 | 68.6 | 68.2 | 65.7 |
| 3 | 74.4 | 65.7 | 57.4 | 59.6 |
| 4 | 68.2 | 61.7 | 70.3 | 70.3 |
| 5 | 61.5 | 67.8 | 70.8 | 69.8 |
| 6 | 68.1 | 69.4 | 70.6 | 69.8 |
| 7 | 68.2 | 66.2 | 67.0 | 69.4 |
| 8 | 63.8 | | | |
| 9 | 68.9 | | | |
| 10 | 70.0 | | | |
| 11 | 70.0 | | | |
| 12 | 70.0 | | | |
| 13 | 64.5 | | | |
| 14 | 70.4 | | | |
| 15 | 72.5 | | | |
| 16 | 72.2 | | | |
| 17 | 73.1 | | | |
| 18 | 68.0 | | | |
| 19 | 74.7 | | | |

TABLE 10

Compositions of Ni—Co—Nb oxide mixtures

| | | 1 | 2 | 3 | 4 | 5 | 6 | 7 | 8 | 9 | 10 | 11 |
|---|---|---|---|---|---|---|---|---|---|---|---|---|
| | | | | | Mole Fraction & Sample Mass, mg | | | | | | | |
| 1 | Ni | 1.00 | | | | | | | | | | |
| | Co | 0.00 | | | | | | | | | | |
| | Nb | 0.00 | | | | | | | | | | |
| | M | 25.8 | | | | | | | | | | |
| 2 | Ni | 0.90 | 0.90 | | | | | | | | | |
| | Co | 0.00 | 0.10 | | | | | | | | | |
| | Nb | 0.10 | 0.00 | | | | | | | | | |
| | M | 29.5 | 31.0 | | | | | | | | | |
| 3 | Ni | 0.80 | 0.80 | 0.80 | | | | | | | | |
| | Co | 0.00 | 0.10 | 0.20 | | | | | | | | |
| | Nb | 0.20 | 0.10 | 0.00 | | | | | | | | |
| | M | 24.6 | 24.5 | 34.4 | | | | | | | | |
| 4 | Ni | 0.70 | 0.70 | 0.70 | 0.70 | | | | | | | |
| | Co | 0.00 | 0.10 | 0.20 | 0.30 | | | | | | | |
| | Nb | 0.30 | 0.20 | 0.10 | 0.00 | | | | | | | |
| | M | 26.4 | 37.0 | 30.3 | 29.9 | | | | | | | |
| 5 | Ni | 0.60 | 0.60 | 0.60 | 0.60 | 0.60 | | | | | | |
| | Co | 0.00 | 0.10 | 0.20 | 0.30 | 0.40 | | | | | | |
| | Nb | 0.40 | 0.30 | 0.20 | 0.10 | 0.00 | | | | | | |
| | M | 33.1 | 34.4 | 35.5 | 38.8 | 31.4 | | | | | | |
| 6 | Ni | 0.50 | 0.50 | 0.50 | 0.50 | 0.50 | 0.50 | | | | | |
| | Co | 0.00 | 0.10 | 0.20 | 0.30 | 0.40 | 0.50 | | | | | |
| | Nb | 0.50 | 0.40 | 0.30 | 0.20 | 0.10 | 0.00 | | | | | |
| | M | 34.4 | 32.7 | 30.8 | 39.4 | 30.4 | 35.5 | | | | | |
| 7 | Ni | 0.40 | 0.40 | 0.40 | 0.40 | 0.40 | 0.40 | 0.40 | | | | |
| | Co | 0.00 | 0.10 | 0.20 | 0.30 | 0.40 | 0.50 | 0.60 | | | | |
| | Nb | 0.60 | 0.50 | 0.40 | 0.30 | 0.20 | 0.10 | 0.00 | | | | |
| | M | 34.6 | 37.5 | 30.1 | 30.4 | 34.3 | 32.3 | 30.9 | | | | |
| 8 | Ni | 0.30 | 0.30 | 0.30 | 0.30 | 0.30 | 0.30 | 0.30 | 0.30 | | | |
| | Co | 0.00 | 0.10 | 0.20 | 0.30 | 0.40 | 0.50 | 0.60 | 0.70 | | | |
| | Nb | 0.70 | 0.60 | 0.50 | 0.40 | 0.30 | 0.20 | 0.10 | 0.00 | | | |
| | M | 42.7 | 32.9 | 35.7 | 29.5 | 28.6 | 36.8 | 38.4 | 26.9 | | | |
| 9 | Ni | 0.20 | 0.20 | 0.20 | 0.20 | 0.20 | 0.20 | 0.20 | 0.20 | 0.20 | | |
| | Co | 0.00 | 0.10 | 0.20 | 0.30 | 0.40 | 0.50 | 0.60 | 0.70 | 0.80 | | |
| | Nb | 0.80 | 0.70 | 0.60 | 0.50 | 0.40 | 0.30 | 0.20 | 0.10 | 0.00 | | |
| | M | 35.3 | 40.7 | 30.8 | 33.2 | 31.2 | 30.3 | 33.0 | 29.6 | 40.7 | | |
| 10 | Ni | 0.10 | 0.10 | 0.10 | 0.10 | 0.10 | 0.10 | 0.10 | 0.10 | 0.10 | 0.10 | |
| | Co | 0.00 | 0.10 | 0.20 | 0.30 | 0.40 | 0.50 | 0.60 | 0.70 | 0.80 | 0.90 | |
| | Nb | 0.90 | 0.80 | 0.70 | 0.60 | 0.50 | 0.40 | 0.30 | 0.20 | 0.10 | 0.00 | |
| | M | 34.4 | 33.2 | 53.4 | 32.7 | 28.8 | 25.0 | 22.8 | 35.6 | 31.0 | 25.6 | |

TABLE 10-continued

Compositions of Ni—Co—Nb oxide mixtures

Mole Fraction & Sample Mass, mg

|    |    | 1 | 2 | 3 | 4 | 5 | 6 | 7 | 8 | 9 | 10 | 11 |
|----|----|---|---|---|---|---|---|---|---|---|----|----|
| 11 | Ni | 0.00 | 0.00 | 0.00 | 0.00 | 0.00 | 0.00 | 0.00 | 0.00 | 0.00 | 0.00 | 0.00 |
|    | Co | 0.00 | 0.10 | 0.20 | 0.30 | 0.40 | 0.50 | 0.60 | 0.70 | 0.80 | 0.90 | 1.00 |
|    | Nb | 1.00 | 0.90 | 0.80 | 0.70 | 0.60 | 0.50 | 0.40 | 0.30 | 0.20 | 0.10 | 0.00 |
|    | M  | 36.6 | 31.0 | 38.7 | 32.0 | 45.2 | 35.1 | 41.0 | 37.0 | 29.1 | 29.6 | 29.0 |

TABLE 11

Ethane conversion of Ni—Co—Nb oxide mixtures listed in Table 10

Ethane Conversion, %

|    | 1 | 2 | 3 | 4 | 5 | 6 | 7 | 8 | 9 | 10 | 11 |
|----|---|---|---|---|---|---|---|---|---|----|----|
| 1  | 2.9 | | | | | | | | | | |
| 2  | 5.4 | 7.1 | | | | | | | | | |
| 3  | 7.4 | 7.9 | 8.3 | | | | | | | | |
| 4  | 7.2 | 11.3 | 8.6 | 8.8 | | | | | | | |
| 5  | 5.6 | 10.2 | 9.4 | 8.5 | 8.1 | | | | | | |
| 6  | 3.4 | 9.3 | 8.5 | 8.6 | 7.8 | 8.1 | | | | | |
| 7  | 1.2 | 7.7 | 8.4 | 8.4 | 8.6 | 8.9 | 10.1 | | | | |
| 8  | 0.3 | 4.2 | 8.7 | 8.6 | 8.4 | 9.7 | 8.2 | 8.1 | | | |
| 9  | 0.3 | 15.0 | 5.5 | 9.1 | 7.2 | 7.4 | 7.3 | 7.8 | 6.9 | | |
| 10 | 0.2 | 1.2 | 1.5 | 7.3 | 7.2 | 7.3 | 7.7 | 8.2 | 8.4 | 9.7 | |
| 11 | 0.1 | 1.4 | 2.2 | 3.0 | 6.1 | 6.3 | 6.7 | 6.7 | 8.6 | 6.6 | 6.7 |

TABLE 12

Ethylene selectivity of Ni—Co—Nb oxide mixtures listed in Table 10

Ethylene Selectivity, %

|    | 1 | 2 | 3 | 4 | 5 | 6 | 7 | 8 | 9 | 10 | 11 |
|----|---|---|---|---|---|---|---|---|---|----|----|
| 1  | 21.0 | | | | | | | | | | |
| 2  | 62.9 | 33.8 | | | | | | | | | |
| 3  | 66.9 | 56.5 | 36.8 | | | | | | | | |
| 4  | 73.6 | 65.1 | 44.9 | 27.9 | | | | | | | |
| 5  | 78.9 | 53.0 | 47.5 | 40.4 | 31.8 | | | | | | |
| 6  | 77.6 | 50.2 | 38.8 | 40.4 | 35.9 | 30.1 | | | | | |
| 7  | 79.7 | 46.9 | 35.0 | 33.5 | 34.7 | 34.2 | 24.7 | | | | |
| 8  | 79.0 | 45.7 | 34.2 | 29.9 | 30.3 | 28.1 | 36.2 | 32.7 | | | |
| 9  | 80.3 | 3.3 | 32.1 | 24.4 | 29.1 | 31.6 | 35.2 | 34.6 | 34.6 | | |
| 10 | 73.4 | 58.6 | 51.3 | 21.4 | 26.4 | 27.4 | 32.9 | 35.7 | 34.9 | 29.4 | |
| 11 | 41.8 | 27.9 | 28.5 | 23.4 | 19.8 | 22.5 | 22.5 | 22.1 | 17.1 | 19.5 | 17.5 |

TABLE 13

Composition and mass of Ni—Co—Nb oxide mixtures

Mole Fraction & Sample Mass, mg

|   |    | 1 | 2 | 3 | 4 | 5 | 6 | 7 | 8 |
|---|----|---|---|---|---|---|---|---|---|
| 1 | Ni | 1.00 | | | | | | | |
|   | Co | 0.00 | | | | | | | |
|   | Nb | 0.00 | | | | | | | |
|   | m  | 44.8 | | | | | | | |
| 2 | Ni | 0.92 | 0.96 | | | | | | |
|   | Co | 0.00 | 0.04 | | | | | | |
|   | Nb | 0.08 | 0.00 | | | | | | |
|   | m  | 36.6 | 34.7 | | | | | | |
| 3 | Ni | 0.85 | 0.88 | 0.92 | | | | | |
|   | Co | 0.00 | 0.04 | 0.08 | | | | | |
|   | Nb | 0.15 | 0.08 | 0.00 | | | | | |
|   | m  | 37.2 | 33.9 | 34.0 | | | | | |
| 4 | Ni | 0.77 | 0.81 | 0.84 | 0.88 | | | | |
|   | Co | 0.00 | 0.04 | 0.08 | 0.12 | | | | |
|   | Nb | 0.23 | 0.16 | 0.08 | 0.00 | | | | |
|   | m  | 40.8 | 35.8 | 35.8 | 42.2 | | | | |
| 5 | Ni | 0.70 | 0.73 | 0.76 | 0.80 | 0.83 | | | |
|   | Co | 0.00 | 0.04 | 0.08 | 0.12 | 0.17 | | | |
|   | Nb | 0.30 | 0.23 | 0.16 | 0.09 | 0.00 | | | |
|   | m  | 33.3 | 38.3 | 46.8 | 45.9 | 20.2 | | | |
| 6 | Ni | 0.63 | 0.65 | 0.68 | 0.71 | 0.75 | 0.78 | | |
|   | Co | 0.00 | 0.04 | 0.08 | 0.12 | 0.17 | 0.22 | | |
|   | Nb | 0.37 | 0.31 | 0.24 | 0.17 | 0.09 | 0.00 | | |
|   | m  | 37.0 | 32.4 | 37.7 | 32.4 | 48.5 | 43.0 | | |
| 7 | Ni | 0.55 | 0.58 | 0.60 | 0.63 | 0.66 | 0.69 | 0.73 | |
|   | Co | 0.00 | 0.04 | 0.08 | 0.12 | 0.16 | 0.22 | 0.27 | |
|   | Nb | 0.45 | 0.39 | 0.32 | 0.25 | 0.18 | 0.09 | 0.00 | |
|   | m  | 48.9 | 38.3 | 30.2 | 32.4 | 32.5 | 40.6 | 36.9 | |
| 8 | Ni | 0.48 | 0.50 | 0.52 | 0.55 | 0.57 | 0.60 | 0.63 | 0.67 |
|   | Co | 0.00 | 0.04 | 0.07 | 0.12 | 0.16 | 0.21 | 0.27 | 0.33 |
|   | Nb | 0.52 | 0.46 | 0.40 | 0.33 | 0.26 | 0.18 | 0.10 | 0.00 |
|   | m  | 41.5 | 36.8 | 35.8 | 28.3 | 37.1 | 34.5 | 38.1 | 40.4 |

TABLE 14

Ethane conversion of Ni—Co—Nb oxide mixtures listed in Table 13

| | 1 | 2 | 3 | 4 | 5 | 6 | 7 | 8 |
|---|---|---|---|---|---|---|---|---|
| | | | | Ethane Conversion, % | | | | |
| 1 | 4.6 | | | | | | | |
| 2 | 2.1 | 6.5 | | | | | | |
| 3 | 5.1 | 4.7 | 6.9 | | | | | |
| 4 | 8.7 | 11.2 | 7.2 | 6.7 | | | | |
| 5 | 9.2 | 12.1 | 6.2 | 8.6 | 6.5 | | | |
| 6 | 10.0 | 13.1 | 12.9 | 10.8 | 8.8 | 7.2 | | |
| 7 | 11.6 | 14.6 | 10.1 | 10.3 | 8.4 | 8.0 | 6.8 | |
| 8 | 7.5 | 13.2 | 10.0 | 8.8 | 8.7 | 7.7 | 9.0 | 7.4 |

TABLE 15

Ethylene selectivity of Ni—Co—Nb oxide mixtures listed in Table 13

| | 1 | 2 | 3 | 4 | 5 | 6 | 7 | 8 |
|---|---|---|---|---|---|---|---|---|
| | | | | Ethylene Selectivity, % | | | | |
| 1 | 16.7 | | | | | | | |
| 2 | 74.9 | 32.0 | | | | | | |
| 3 | 83.8 | 62.8 | 35.0 | | | | | |
| 4 | 85.1 | 82.4 | 54.5 | 33.5 | | | | |
| 5 | 81.3 | 84.1 | 74.3 | 58.4 | 31.7 | | | |
| 6 | 85.3 | 72.4 | 79.2 | 66.7 | 52.4 | 29.8 | | |
| 7 | 85.7 | 75.9 | 68.5 | 59.7 | 46.3 | 37.8 | 27.2 | |
| 8 | 78.3 | 76.7 | 56.9 | 52.9 | 50.8 | 36.3 | 29.3 | 31.5 |

TABLE 16

Composition and mass of Ni—Nb—Ta—K oxide mixtures

| | | 1 | 2 | 3 | 4 | 5 | 6 | 7 |
|---|---|---|---|---|---|---|---|---|
| | | | | Mole Fraction & Sample Mass, mg | | | | |
| 1 | Ni | 0.5837 | | | | | | |
| | Nb | 0.3772 | | | | | | |
| | Ta | 0.0391 | | | | | | |
| | K | 0.0000 | | | | | | |
| | M | 38.7 | | | | | | |
| 2 | Ni | 0.5910 | 0.5916 | | | | | |
| | Nb | 0.3289 | 0.3292 | | | | | |
| | Ta | 0.0396 | 0.0792 | | | | | |
| | K | 0.0405 | 0.0000 | | | | | |
| | M | 35.4 | 38.4 | | | | | |
| 3 | Ni | 0.5985 | 0.5991 | 0.5997 | | | | |
| | Nb | 0.2793 | 0.2796 | 0.2799 | | | | |
| | Ta | 0.0401 | 0.0802 | 0.1204 | | | | |
| | K | 0.0821 | 0.0411 | 0.0000 | | | | |
| | M | 37.7 | 38.0 | 42.0 | | | | |
| 4 | Ni | 0.6062 | 0.6068 | 0.6074 | 0.6080 | | | |
| | Nb | 0.2285 | 0.2287 | 0.2290 | 0.2292 | | | |
| | Ta | 0.0406 | 0.0812 | 0.1220 | 0.1628 | | | |
| | K | 0.1247 | 0.0832 | 0.0417 | 0.0000 | | | |
| | M | 43.1 | 40.6 | 38.7 | 40.8 | | | |
| 5 | Ni | 0.6141 | 0.6147 | 0.6153 | 0.6160 | 0.6166 | | |
| | Nb | 0.1764 | 0.1765 | 0.1767 | 0.1769 | 0.1771 | | |
| | Ta | 0.0411 | 0.0823 | 0.1235 | 0.1649 | 0.2063 | | |
| | K | 0.1685 | 0.1265 | 0.0844 | 0.0422 | 0.0000 | | |
| | M | 36.4 | 36.5 | 42.3 | 40.1 | 39.0 | | |
| 6 | Ni | 0.6222 | 0.6228 | 0.6235 | 0.6241 | 0.6247 | 0.6254 | |
| | Nb | 0.1228 | 0.1230 | 0.1231 | 0.1232 | 0.1233 | 0.1235 | |
| | Ta | 0.0416 | 0.0834 | 0.1252 | 0.1671 | 0.2091 | 0.2511 | |
| | K | 0.2134 | 0.1709 | 0.1283 | 0.0856 | 0.0429 | 0.0000 | |
| | M | 36.9 | 41.5 | 36.1 | 44.4 | 40.2 | 39.3 | |
| 7 | Ni | 0.6305 | 0.6311 | 0.6318 | 0.6324 | 0.6331 | 0.6338 | 0.6345 |
| | Nb | 0.0679 | 0.0680 | 0.0680 | 0.0681 | 0.0682 | 0.0683 | 0.0683 |
| | Ta | 0.0422 | 0.0845 | 0.1268 | 0.1693 | 0.2119 | 0.2545 | 0.2972 |
| | K | 0.2595 | 0.2164 | 0.1733 | 0.1301 | 0.0869 | 0.0435 | 0.0000 |
| | M | 39.7 | 40.4 | 38.8 | 51.4 | 45.6 | 42.9 | 43.9 |

TABLE 17

Ethane conversion of Ni—Nb—Ta—K oxide mixtures listed in Table 16

| | 1 | 2 | 3 | 4 | 5 | 6 | 7 |
|---|---|---|---|---|---|---|---|
| | | | | Ethane Conversion, % | | | |
| 1 | 6.3 | | | | | | |
| 2 | 4.9 | 6.0 | | | | | |
| 3 | 4.5 | 5.3 | 6.3 | | | | |
| 4 | 4.4 | 4.5 | 5.7 | 7.0 | | | |
| 5 | 3.0 | 4.4 | 5.1 | 6.1 | 6.5 | | |
| 6 | 0.8 | 2.7 | 3.8 | 5.1 | 5.4 | 6.5 | |
| 7 | 0.3 | 0.9 | 2.3 | 4.2 | 5.1 | 6.3 | 5.8 |

TABLE 18

Ethylene Selectivity of Ni—Nb—Ta—K oxide mixtures listed in Table 16 at 300° C.

| | 1 | 2 | 3 | 4 | 5 | 6 | 7 |
|---|---|---|---|---|---|---|---|
| | | | | Ethylene Selectivity, % | | | |
| 1 | 80.6 | | | | | | |
| 2 | 62.3 | 84.8 | | | | | |
| 3 | 45.5 | 68.4 | 85.2 | | | | |
| 4 | 34.4 | 49.4 | 73.1 | 84.6 | | | |
| 5 | 16.3 | 35.4 | 55.4 | 76.9 | 85.9 | | |
| 6 | 1.3 | 17.4 | 37.2 | 54.6 | 80.9 | 85.2 | |
| 7 | 0.0 | 1.0 | 8.7 | 39.1 | 59.1 | 78.3 | 86.9 |

TABLE 19

Composition and mass of bulk Ni—Nb—Ta oxide mixtures

Mole Fraction & Sample Mass, mg

| | | 1 | 2 | 3 | 4 | 5 | 6 | 7 |
|---|---|---|---|---|---|---|---|---|
| 1 | Ni | 0.95 | | | | | | |
| | Nb | 0.03 | | | | | | |
| | Ta | 0.02 | | | | | | |
| | M | 28.2 | | | | | | |
| 2 | Ni | 0.91 | 0.89 | | | | | |
| | Nb | 0.03 | 0.09 | | | | | |
| | Ta | 0.06 | 0.02 | | | | | |
| | M | 43.7 | 51.8 | | | | | |
| 3 | Ni | 0.87 | 0.85 | 0.83 | | | | |
| | Nb | 0.03 | 0.09 | 0.15 | | | | |
| | Ta | 0.10 | 0.06 | 0.02 | | | | |
| | M | 47.6 | 35.2 | 39.2 | | | | |
| 4 | Ni | 0.82 | 0.80 | 0.78 | 0.77 | | | |
| | Nb | 0.04 | 0.10 | 0.16 | 0.21 | | | |
| | Ta | 0.14 | 0.10 | 0.06 | 0.02 | | | |
| | M | 53.1 | 40.5 | 38.8 | 35.8 | | | |
| 5 | Ni | 0.78 | 0.76 | 0.74 | 0.72 | 0.70 | | |
| | Nb | 0.04 | 0.10 | 0.16 | 0.22 | 0.27 | | |
| | Ta | 0.19 | 0.14 | 0.10 | 0.06 | 0.02 | | |
| | M | 39.8 | 52.1 | 38.1 | 37.5 | 36.8 | | |
| 6 | Ni | 0.73 | 0.71 | 0.69 | 0.67 | 0.66 | 0.64 | |
| | Nb | 0.04 | 0.10 | 0.17 | 0.23 | 0.28 | 0.34 | |
| | Ta | 0.24 | 0.19 | 0.14 | 0.10 | 0.06 | 0.02 | |
| | M | 70.1 | 42.4 | 37.1 | 40.2 | 37.0 | 39.6 | |
| 7 | Ni | 0.67 | 0.66 | 0.64 | 0.62 | 0.61 | 0.59 | 0.58 |
| | Nb | 0.04 | 0.11 | 0.17 | 0.23 | 0.29 | 0.35 | 0.40 |
| | Ta | 0.29 | 0.24 | 0.19 | 0.14 | 0.10 | 0.06 | 0.02 |
| | M | 35.6 | 45.2 | 36.1 | 42.0 | 35.6 | 36.1 | 38.2 |

TABLE 20

Ethane conversion of Ni—Nb—Ta oxide mixtures listed in Table 19

Ethane Conversion, %

| | 1 | 2 | 3 | 4 | 5 | 6 | 7 |
|---|---|---|---|---|---|---|---|
| 1 | 2.0 | | | | | | |
| 2 | 4.1 | 3.8 | | | | | |
| 3 | 3.8 | 6.1 | 7.9 | | | | |
| 4 | 4.1 | 2.6 | 5.3 | 6.1 | | | |
| 5 | 2.8 | 3.8 | 4.5 | 6.9 | 6.4 | | |
| 6 | 5.4 | 3.2 | 6.6 | 3.3 | 7.1 | 6.4 | |
| 7 | 3.9 | 3.9 | 5.2 | 3.7 | 5.3 | 7.0 | 6.1 |

TABLE 21

Ethylene selectivity of Ni—Nb—Ta oxide mixtures listed in Table 19

Ethylene Selectivity, %

| | 1 | 2 | 3 | 4 | 5 | 6 | 7 |
|---|---|---|---|---|---|---|---|
| 1 | 70.8 | | | | | | |
| 2 | 69.3 | 63.4 | | | | | |
| 3 | 68.5 | 74.3 | 68.4 | | | | |
| 4 | 61.9 | 62.0 | 74.5 | 69.9 | | | |
| 5 | 59.8 | 67.4 | 69.7 | 74.6 | 76.5 | | |
| 6 | 74.9 | 65.2 | 76.0 | 67.2 | 76.4 | 75.8 | |
| 7 | 75.5 | 67.3 | 73.0 | 72.1 | 72.2 | 80.0 | 75.3 |

TABLE 22

Composition and mass of Ni—Nb—Ta oxide mixtures

Mole Fraction & Sample Mass, mg

| | | 1 | 2 | 3 | 4 | 5 | 6 | 7 |
|---|---|---|---|---|---|---|---|---|
| 1 | Ni | 0.8621 | | | | | | |
| | Nb | 0.0690 | | | | | | |
| | Ta | 0.0690 | | | | | | |
| | M | 39.3 | | | | | | |
| 2 | Ni | 0.8128 | 0.8128 | | | | | |
| | Nb | 0.0725 | 0.1147 | | | | | |
| | Ta | 0.1147 | 0.0725 | | | | | |
| | M | 35.4 | 38.5 | | | | | |
| 3 | Ni | 0.7583 | 0.7583 | 0.7583 | | | | |
| | Nb | 0.0763 | 0.1208 | 0.1654 | | | | |
| | Ta | 0.1654 | 0.1208 | 0.0763 | | | | |
| | M | 43.7 | 43.2 | 39.7 | | | | |
| 4 | Ni | 0.6977 | 0.6977 | 0.6977 | 0.6977 | | | |
| | Nb | 0.0806 | 0.1276 | 0.1747 | 0.2217 | | | |
| | Ta | 0.2217 | 0.1747 | 0.1276 | 0.0806 | | | |
| | M | 50.8 | 38.1 | 38.2 | 36.9 | | | |
| 5 | Ni | 0.6298 | 0.6298 | 0.6298 | 0.6298 | 0.6298 | | |
| | Nb | 0.0854 | 0.1353 | 0.1851 | 0.2349 | 0.2848 | | |
| | Ta | 0.2848 | 0.2349 | 0.1851 | 0.1353 | 0.0854 | | |
| | M | 48.9 | 43.6 | 47.5 | 48.3 | 41.8 | | |
| 6 | Ni | 0.5533 | 0.5533 | 0.5533 | 0.5533 | 0.5533 | 0.5533 | |
| | Nb | 0.0909 | 0.1439 | 0.1969 | 0.2499 | 0.3029 | 0.3559 | |
| | Ta | 0.3559 | 0.3029 | 0.2499 | 0.1969 | 0.1439 | 0.0909 | |
| | M | 28.3 | 48.5 | 46.4 | 47.9 | 40.0 | 56.0 | |
| 7 | Ni | 0.4664 | 0.4664 | 0.4664 | 0.4664 | 0.4664 | 0.4664 | 0.4664 |
| | Nb | 0.0970 | 0.1536 | 0.2102 | 0.2668 | 0.3234 | 0.3800 | 0.4366 |
| | Ta | 0.4366 | 0.3800 | 0.3234 | 0.2668 | 0.2102 | 0.1536 | 0.0970 |
| | M | 51.8 | 34.1 | 49.2 | 35.7 | 42.5 | 47.5 | 62.7 |

TABLE 23

Ethane Conversion at 300° C. of Ni—Nb—Ta oxide mixtures listed in Table 22

| | 1 | 2 | 3 | 4 | 5 | 6 | 7 |
|---|---|---|---|---|---|---|---|
| | | | | Ethane Conversion, % | | | |
| 1 | 9.6 | | | | | | |
| 2 | 10.2 | 10.1 | | | | | |
| 3 | 10.6 | 10.9 | 8.2 | | | | |
| 4 | 11.1 | 9.9 | 9.1 | 8.2 | | | |
| 5 | 9.6 | 10.0 | 10.4 | 10.2 | 9.9 | | |
| 6 | 4.5 | 7.2 | 7.1 | 7.2 | 7.1 | 8.9 | |
| 7 | 1.4 | 2.0 | 1.8 | 0.7 | 1.1 | 2.5 | 1.4 |

TABLE 24

Ethylene selectivity at 300° C. of Ni—Nb—Ta oxide mixtures listed in Table 22

| | 1 | 2 | 3 | 4 | 5 | 6 | 7 |
|---|---|---|---|---|---|---|---|
| | | | | Ethylene Selectivity, % | | | |
| 1 | 80.4 | | | | | | |
| 2 | 80.1 | 82.8 | | | | | |
| 3 | 84.0 | 84.5 | 84.5 | | | | |
| 4 | 81.8 | 84.0 | 82.7 | 84.3 | | | |
| 5 | 86.8 | 84.6 | 86.3 | 86.9 | 87.0 | | |
| 6 | 84.2 | 88.1 | 89.1 | 87.2 | 87.6 | 90.1 | |
| 7 | 82.5 | 84.7 | 86.6 | 79.4 | 86.6 | 87.8 | 80.5 |

TABLE 25

Ethane Conversion at 325° C. of Ni—Nb—Ta oxide mixtures listed in Table 22

| | 1 | 2 | 3 | 4 | 5 | 6 | 7 |
|---|---|---|---|---|---|---|---|
| | | | | Ethane Conversion, % | | | |
| 1 | 14.6 | | | | | | |
| 2 | 15.9 | 14.5 | | | | | |
| 3 | 15.2 | 16.0 | 12.6 | | | | |
| 4 | 15.9 | 14.5 | 13.6 | 12.7 | | | |
| 5 | 14.3 | 15.5 | 15.4 | 15.2 | 14.8 | | |
| 6 | 8.2 | 11.8 | 11.4 | 11.6 | 11.8 | 13.9 | |
| 7 | 2.5 | 3.9 | 3.4 | 1.4 | 1.9 | 5.0 | 2.7 |

TABLE 26

Ethylene selectivity at 325° C. of Ni—Nb—Ta oxide mixtures listed in Table 22

| | 1 | 2 | 3 | 4 | 5 | 6 | 7 |
|---|---|---|---|---|---|---|---|
| | | | | Ethylene Selectivity, % | | | |
| 1 | 84.2 | | | | | | |
| 2 | 81.7 | 84.5 | | | | | |
| 3 | 83.9 | 84.9 | 84.3 | | | | |
| 4 | 82.5 | 86.0 | 83.4 | 84.6 | | | |
| 5 | 87.8 | 86.8 | 85.9 | 86.8 | 87.8 | | |
| 6 | 83.8 | 87.5 | 88.2 | 87.8 | 86.1 | 88.9 | |
| 7 | 81.5 | 84.2 | 86.0 | 77.2 | 85.2 | 86.4 | 78.5 |

TABLE 27

Difference in ethylene concentration between reactor effluent and feed for Ni—Nb—Ta oxide mixtures listed in Table 22 ($C_2H_6/C_2H_4$ Feed)

| | 1 | 2 | 3 | 4 | 5 | 6 | 7 |
|---|---|---|---|---|---|---|---|
| | | | | $\Delta\ CH_4$, % | | | |
| 1 | 7.0 | | | | | | |
| 2 | 7.2 | 6.2 | | | | | |
| 3 | 5.1 | 6.4 | 5.0 | | | | |
| 4 | 6.8 | 6.6 | 4.7 | 5.3 | | | |
| 5 | 7.3 | 7.3 | 5.9 | 7.1 | 7.1 | | |
| 6 | 4.0 | 5.6 | 5.4 | 5.7 | 5.3 | 6.1 | |
| 7 | 1.2 | 2.0 | 1.4 | −0.4 | 0.8 | 2.2 | 1.0 |

TABLE 28

Difference in ethane concentration between reactor effluent and feed for Ni—Nb—Ta oxide mixtures listed in Table 22 ($C_2H_6/C_2H_4$ Feed)

| | 1 | 2 | 3 | 4 | 5 | 6 | 7 |
|---|---|---|---|---|---|---|---|
| | | | | $\Delta\ C_2H_6$, % | | | |
| 1 | −9.3 | | | | | | |
| 2 | −10.5 | −8.3 | | | | | |
| 3 | −8.1 | −9.3 | −7.4 | | | | |
| 4 | −9.9 | −8.6 | −7.2 | −7.5 | | | |
| 5 | −8.9 | −9.3 | −8.4 | −9.4 | −8.8 | | |
| 6 | −5.3 | −7.1 | −6.8 | −7.1 | −7.3 | −7.9 | |
| 7 | −1.3 | −2.3 | −1.7 | 0.4 | −0.8 | −2.9 | −1.3 |

TABLE 29

Difference in carbon monoxide and carbon dioxide between reactor effluent and feed for Ni—Nb—Ta oxide mixtures listed in Table 22 ($C_2H_6/C_2H_4$ Feed)

| | 1 | 2 | 3 | 4 | 5 | 6 | 7 |
|---|---|---|---|---|---|---|---|
| | | | | $\Delta\ CO\ \&\ CO_2$, % | | | |
| 1 | 2.2 | | | | | | |
| 2 | 3.3 | 2.2 | | | | | |
| 3 | 2.9 | 2.9 | 2.4 | | | | |
| 4 | 3.1 | 1.9 | 2.5 | 2.2 | | | |
| 5 | 1.7 | 1.9 | 2.5 | 2.3 | 1.8 | | |
| 6 | 1.3 | 1.5 | 1.4 | 1.4 | 1.9 | 1.8 | |
| 7 | 0.1 | 0.3 | 0.3 | 0.0 | 0.0 | 0.7 | 0.3 |

TABLE 30

Composition and mass of Ni—Nb—Ta oxide mixtures

| | | 1 | 2 | 3 | 4 | 5 | 6 |
|---|---|---|---|---|---|---|---|
| | | | | Mole Fraction & Sample Mass, mg | | | |
| 1 | Ni | 0.7194 | 0.7196 | 0.7197 | 0.7199 | 0.7201 | 0.7202 |
| | Nb | 0.2324 | 0.1937 | 0.1550 | 0.1163 | 0.0775 | 0.0388 |
| | Ta | 0.0481 | 0.0867 | 0.1252 | 0.1638 | 0.2024 | 0.2410 |
| | M | 44.6 | 42.8 | 38.4 | 37.1 | 48.8 | 41.5 |
| 2 | Ni | 0.6959 | 0.6960 | 0.6962 | 0.6964 | 0.6965 | 0.6967 |
| | Nb | 0.2519 | 0.2100 | 0.1680 | 0.1261 | 0.0841 | 0.0420 |
| | Ta | 0.0522 | 0.0940 | 0.1358 | 0.1776 | 0.2194 | 0.2613 |
| | M | 40.1 | 40.5 | 39.0 | 36.8 | 44.4 | 49.9 |
| 3 | Ni | 0.6680 | 0.6682 | 0.6683 | 0.6685 | 0.6687 | 0.6689 |
| | Nb | 0.2750 | 0.2293 | 0.1835 | 0.1376 | 0.0918 | 0.0459 |
| | Ta | 0.0570 | 0.1026 | 0.1482 | 0.1939 | 0.2395 | 0.2852 |
| | M | 35.6 | 37.0 | 40.7 | 41.0 | 44.2 | 51.9 |
| 4 | Ni | 0.6345 | 0.6346 | 0.6348 | 0.6350 | 0.6352 | 0.6354 |
| | Nb | 0.3028 | 0.2524 | 0.2020 | 0.1515 | 0.1011 | 0.0505 |
| | Ta | 0.0627 | 0.1129 | 0.1632 | 0.2135 | 0.2638 | 0.3141 |
| | M | 37.9 | 38.6 | 37.0 | 34.8 | 35.9 | 36.4 |

TABLE 30-continued

Composition and mass of Ni—Nb—Ta oxide mixtures

Mole Fraction & Sample Mass, mg

|   |    | 1 | 2 | 3 | 4 | 5 | 6 |
|---|----|---|---|---|---|---|---|
| 5 | Ni | 0.5934 | 0.5936 | 0.5938 | 0.5940 | 0.5942 | 0.5944 |
|   | Nb | 0.3368 | 0.2808 | 0.2247 | 0.1686 | 0.1124 | 0.0562 |
|   | Ta | 0.0698 | 0.1256 | 0.1815 | 0.2374 | 0.2934 | 0.3494 |
|   | M  | 36.5 | 36.0 | 36.6 | 41.5 | 35.6 | 35.4 |
| 6 | Ni | 0.5420 | 0.5422 | 0.5424 | 0.5426 | 0.5428 | 0.5430 |
|   | Nb | 0.3794 | 0.3163 | 0.2531 | 0.1899 | 0.1267 | 0.0633 |
|   | Ta | 0.0786 | 0.1414 | 0.2045 | 0.2675 | 0.3306 | 0.3937 |
|   | M  | 36.8 | 38.1 | 39.9 | 39.2 | 33.9 | 35.8 |

TABLE 31

Ethane Conversion at 300° C. of Ni—Nb—Ta oxide mixtures listed in Table 30

Ethane Conversion, %

|   | 1 | 2 | 3 | 4 | 5 | 6 |
|---|---|---|---|---|---|---|
| 1 | 5.8 | 3.8 | 3.3 | 4.3 | 5.2 | 4.1 |
| 2 | 3.8 | 4.4 | 4.5 | 3.8 | 3.9 | 3.7 |
| 3 | 7.5 | 9.6 | 10.3 | 7.6 | 6.1 | 6.9 |
| 4 | 7.8 | 7.5 | 8.4 | 9.1 | 9.8 | 9.9 |
| 5 | 8.5 | 8.1 | 8.2 | 8.9 | 9.2 | 10.2 |
| 6 | 9.6 | 9.1 | 10.3 | 10.4 | 10.7 | 11.6 |

TABLE 32

Ethylene selectivity at 300° C. of Ni—Nb—Ta oxide mixtures listed in Table 30

Ethylene Selectivity, %

|   | 1 | 2 | 3 | 4 | 5 | 6 |
|---|---|---|---|---|---|---|
| 1 | 87.2 | 88.0 | 88.2 | 89.4 | 89.3 | 89.6 |
| 2 | 86.4 | 87.1 | 89.2 | 90.4 | 87.3 | 87.7 |
| 3 | 85.1 | 84.4 | 81.8 | 85.4 | 90.5 | 89.0 |
| 4 | 82.8 | 84.0 | 85.2 | 85.4 | 83.5 | 83.8 |
| 5 | 80.2 | 83.1 | 84.6 | 85.0 | 85.5 | 85.9 |
| 6 | 77.5 | 78.1 | 81.5 | 84.1 | 83.3 | 85.3 |

TABLE 33

Ethane conversion at 325° C. of Ni—Nb—Ta oxide mixtures listed in Table 30

Ethane Conversion, %

|   | 1 | 2 | 3 | 4 | 5 | 6 |
|---|---|---|---|---|---|---|
| 1 | 8.7 | 6.7 | 5.7 | 7.3 | 8.8 | 6.8 |
| 2 | 6.7 | 7.3 | 7.2 | 6.2 | 6.5 | 6.3 |
| 3 | 11.7 | 13.3 | 13.9 | 11.5 | 9.6 | 11.1 |
| 4 | 12.2 | 11.7 | 12.2 | 12.8 | 14.0 | 14.4 |
| 5 | 12.8 | 12.0 | 13.0 | 13.7 | 14.0 | 15.4 |
| 6 | 14.1 | 14.0 | 15.9 | 15.6 | 16.5 | 16.9 |

TABLE 34

Ethylene selectivity at 325° C. of Ni—Nb—Ta oxide mixtures listed in Table 30

Ethylene Selectivity

|   | 1 | 2 | 3 | 4 | 5 | 6 |
|---|---|---|---|---|---|---|
| 1 | 85.7 | 85.6 | 85.9 | 86.8 | 87.5 | 88.6 |
| 2 | 84.4 | 85.1 | 86.3 | 88.1 | 85.6 | 85.6 |
| 3 | 84.3 | 83.7 | 84.9 | 84.8 | 89.4 | 88.0 |
| 4 | 84.0 | 83.8 | 85.4 | 84.0 | 85.2 | 84.5 |
| 5 | 81.3 | 83.9 | 84.1 | 84.5 | 84.5 | 85.9 |
| 6 | 82.3 | 81.4 | 83.5 | 84.2 | 85.0 | 85.8 |

TABLE 35

Difference in ethylene concentration between reactor effluent and feed for Ni—Nb—Ta oxide mixtures listed in Table 30 ($C_2H_6/C_2H_4$ Feed)

$\Delta\ C_2H_4$, %

|   | 1 | 2 | 3 | 4 | 5 | 6 |
|---|---|---|---|---|---|---|
| 1 | 2.3 | 1.1 | 0.6 | 0.4 | 2.3 | 1.8 |
| 2 | 1.2 | 1.2 | 0.5 | 1.2 | 1.5 | 0.9 |
| 3 | 3.1 | 4.6 | 5.6 | 4.2 | 3.7 | 4.2 |
| 4 | 4.6 | 4.1 | 4.4 | 4.2 | 5.5 | 5.4 |
| 5 | 3.7 | 4.2 | 4.6 | 4.6 | 4.0 | 6.1 |
| 6 | 6.0 | 5.3 | 5.9 | 5.0 | 6.8 | 7.0 |

TABLE 36

Difference in ethane concentration between reactor effluent and feed for Ni—Nb—Ta oxide mixtures listed in Table 30 ($C_2H_6/C_2H_4$ Feed)

$\Delta\ C_2H_6$, %

|   | 1 | 2 | 3 | 4 | 5 | 6 |
|---|---|---|---|---|---|---|
| 1 | -3.8 | -2.8 | -2.1 | -2.4 | -4.2 | -3.1 |
| 2 | -2.9 | -3.0 | -2.3 | -2.7 | -2.9 | -2.5 |
| 3 | -5.6 | -7.0 | -8.3 | -6.2 | -5.1 | -5.9 |
| 4 | -6.6 | -6.2 | -6.8 | -6.6 | -7.7 | -7.8 |
| 5 | -6.5 | -6.5 | -6.8 | -7.0 | -6.8 | -9.0 |
| 6 | -8.3 | -8.0 | -8.7 | -8.1 | -9.8 | -9.9 |

TABLE 37

Difference in carbon monoxide and carbon dioxide between reactor effluent and feed for Ni—Nb—Ta oxide mixtures listed in Table 30 ($C_2H_6/C_2H_4$ Feed)

$\Delta\ CO\ \&\ CO_2$, %

|   | 1 | 2 | 3 | 4 | 5 | 6 |
|---|---|---|---|---|---|---|
| 1 | 1.5 | 1.7 | 1.5 | 1.9 | 1.9 | 1.4 |
| 2 | 1.7 | 1.8 | 1.8 | 1.4 | 1.4 | 1.6 |
| 3 | 2.5 | 2.5 | 2.6 | 2.1 | 1.4 | 1.7 |
| 4 | 1.9 | 2.1 | 2.4 | 2.4 | 2.2 | 2.5 |
| 5 | 2.8 | 2.3 | 2.3 | 2.4 | 2.8 | 2.9 |
| 6 | 2.3 | 2.6 | 2.9 | 3.1 | 3.0 | 2.9 |

TABLE 38

Composition and mass of Ni—Nb—Ta oxide mixtures calcined at 300° C.

Mole Fraction & Sample Mass, mg

|   |    | 1 | 2 | 3 | 4 | 5 | 6 |
|---|----|---|---|---|---|---|---|
| 1 | Ni | 1.000 | | | | | |
|   | Nb | 0.000 | | | | | |
|   | Ta | 0.000 | | | | | |
|   | M  | 56.1  | | | | | |

TABLE 38-continued

Composition and mass of Ni—Nb—Ta oxide mixtures calcined at 300° C.

Mole Fraction & Sample Mass, mg

|   |    | 1 | 2 | 3 | 4 | 5 | 6 |
|---|----|---|---|---|---|---|---|
| 2 | Ni | 0.883 | 0.890 | | | | |
|   | Nb | 0.000 | 0.110 | | | | |
|   | Ta | 0.117 | 0.000 | | | | |
|   | M  | 46.0 | 58.0 | | | | |
| 3 | Ni | 0.782 | 0.787 | 0.793 | | | |
|   | Nb | 0.000 | 0.103 | 0.208 | | | |
|   | Ta | 0.218 | 0.110 | 0.000 | | | |
|   | M  | 45.4 | 57.2 | 47.7 | | | |
| 4 | Ni | 0.693 | 0.698 | 0.702 | 0.706 | | |
|   | Nb | 0.000 | 0.097 | 0.195 | 0.294 | | |
|   | Ta | 0.307 | 0.206 | 0.104 | 0.000 | | |
|   | M  | 49.9 | 46.5 | 45.2 | 50.0 | | |
| 5 | Ni | 0.615 | 0.618 | 0.622 | 0.626 | 0.629 | |
|   | Nb | 0.000 | 0.091 | 0.183 | 0.276 | 0.371 | |
|   | Ta | 0.385 | 0.291 | 0.195 | 0.098 | 0.000 | |
|   | M  | 51.5 | 52.0 | 47.5 | 55.3 | 54.2 | |
| 6 | Ni | 0.545 | 0.548 | 0.551 | 0.554 | 0.557 | 0.560 |
|   | Nb | 0.000 | 0.086 | 0.173 | 0.261 | 0.350 | 0.440 |
|   | Ta | 0.455 | 0.366 | 0.276 | 0.185 | 0.093 | 0.000 |
|   | M  | 54.5 | 54.6 | 57.2 | 59.6 | 54.3 | 50.8 |

TABLE 39

Ethane Conversion at 300° C. of Ni—Nb—Ta oxide mixtures listed in Table 38

Ethane Conversion, %

|   | 1 | 2 | 3 | 4 | 5 | 6 |
|---|---|---|---|---|---|---|
| 1 | 10.5 | | | | | |
| 2 | 12.0 | 17.7 | | | | |
| 3 | 18.9 | 19.2 | 15.4 | | | |
| 4 | 18.6 | 18.4 | 20.0 | — | | |
| 5 | 18.6 | 19.9 | 20.0 | 20.5 | 19.0 | |
| 6 | 15.2 | 18.9 | 16.9 | 19.0 | 18.1 | 16.9 |

TABLE 40

Ethylene selectivity at 300° C. of Ni—Nb—Ta oxide mixtures listed in Table 38

Ethylene Selectivity, %

|   | 1 | 2 | 3 | 4 | 5 | 6 |
|---|---|---|---|---|---|---|
| 1 | 53.6 | | | | | |
| 2 | 54.9 | 81.6 | | | | |
| 3 | 83.3 | 83.9 | 77.4 | | | |
| 4 | 83.3 | 84.4 | 85.2 | — | | |
| 5 | 84.4 | 85.1 | 86.1 | 86.2 | 84.7 | |
| 6 | 83.9 | 84.6 | 84.2 | 86.0 | 84.8 | 80.9 |

TABLE 41

Ethane Conversion at 250° C. of Ni—Nb—Ta oxide mixtures listed in Table 38

Ethane Conversion, %

|   | 1 | 2 | 3 | 4 | 5 | 6 |
|---|---|---|---|---|---|---|
| 1 | 5.4 | | | | | |
| 2 | 5.7 | 9.7 | | | | |
| 3 | 9.8 | 11.0 | 5.9 | | | |
| 4 | 9.8 | 4.5 | 5.5 | — | | |
| 5 | 4.6 | 4.5 | 4.6 | 5.1 | 4.5 | |
| 6 | 2.9 | 4.1 | 3.3 | 4.5 | 4.2 | 4.0 |

TABLE 42

Ethylene selectivity at 250° C. of Ni—Nb—Ta oxide mixtures listed in Table 38

Ethylene Selectivity, %

|   | 1 | 2 | 3 | 4 | 5 | 6 |
|---|---|---|---|---|---|---|
| 1 | 27.6 | | | | | |
| 2 | 32.8 | 76.2 | | | | |
| 3 | 79.9 | 79.9 | 68.6 | | | |
| 4 | 78.6 | 77.4 | 81.6 | — | | |
| 5 | 77.5 | 80.4 | 84.4 | 85.0 | 76.4 | |
| 6 | 81.7 | 79.3 | 81.1 | 85.5 | 78.3 | 69.9 |

TABLE 43

Difference in ethylene concentration between reactor effluent and feed for Ni—Nb—Ta oxide mixtures listed in Table 38 ($C_2H_6/C_2H_4$ Feed)

$\Delta\ C_2H_4$, %

|   | 1 | 2 | 3 | 4 | 5 | 6 |
|---|---|---|---|---|---|---|
| 1 | | | | | | |
| 2 | | | | | | |
| 3 | | | | | | |
| 4 | | | 7.3 | 6.3 | | |
| 5 | 6.5 | 7.4 | 6.1 | 6.4 | 7.2 | |
| 6 | 5.4 | 7.1 | 5.2 | 6.0 | 7.0 | 5.6 |

TABLE 44

Difference in ethane concentration between reactor effluent and feed for Ni—Nb—Ta oxide mixtures listed in Table 38 ($C_2H_6/C_2H_4$ Feed)

$\Delta\ C_2H_6$, %

|   | 1 | 2 | 3 | 4 | 5 | 6 |
|---|---|---|---|---|---|---|
| 1 | | | | | | |
| 2 | | | | | | |
| 3 | | | | | | |
| 4 | | -10.3 | -9.8 | | | |
| 5 | -9.7 | -10.8 | -9.3 | -9.7 | -10.3 | |
| 6 | -7.9 | -10.2 | -8.2 | -9.2 | -10.0 | -8.9 |

TABLE 45

Difference in carbon monoxide and carbon dioxide between reactor effluent and feed for Ni—Nb—Ta oxide mixtures listed in Table 38 ($C_2H_6/C_2H_4$ Feed)

$\Delta\ CO\ \&\ CO_2$, %

|   | 1 | 2 | 3 | 4 | 5 | 6 |
|---|---|---|---|---|---|---|
| 1 | | | | | | |
| 2 | | | | | | |
| 3 | | | | | | |
| 4 | | 3.0 | 3.6 | | | |
| 5 | 3.2 | 3.5 | 3.2 | 3.4 | 3.2 | |
| 6 | 2.5 | 3.2 | 3.0 | 3.2 | 3.1 | 3.4 |

TABLE 46

Composition and mass of Ni—Nb, Ni—Co, Ni—Co—Nb, Ni—Nb—Al, Ni—Nb—Fe, and Mo—V—Nb oxide mixtures; difference in ethane and ethylene concentration between reactor effluent and feed; carbon monoxide and carbon dioxide production.

| Sample ID | Δ $C_2H_4$ % | Δ $C_2H_6$ % | Δ CO & $CO_2$, % | m, mg | Mole Fraction Ni | Co | Nb | Al | Fe |
|---|---|---|---|---|---|---|---|---|---|
| MoVNb | −1.1 | −0.4 | 1.8 | 40.8 | | | | | |
| Blank | 0.2 | −0.3 | 0.4 | 0.0 | | | | | |
| 21187.12 | 3.4 | −6.0 | 3.0 | 39.4 | 0.60 | 0.00 | 0.36 | 0.05 | 0.00 |
| 21187.31 | 4.0 | −7.2 | 3.5 | 41.5 | 0.61 | 0.00 | 0.36 | 0.00 | 0.02 |
| 21187.32 | 3.3 | −6.8 | 3.8 | 38.9 | 0.60 | 0.00 | 0.36 | 0.00 | 0.05 |
| 21187.33 | 2.0 | −5.6 | 3.9 | 40.7 | 0.58 | 0.00 | 0.35 | 0.00 | 0.07 |
| 10717.31 | 4.7 | −6.8 | 2.4 | 41.2 | 0.85 | 0.00 | 0.15 | 0.00 | 0.00 |
| 10717.41 | 6.7 | −9.9 | 3.5 | 39.9 | 0.77 | 0.00 | 0.23 | 0.00 | 0.00 |
| 10717.42 | 7.2 | −10.3 | 3.4 | 40.2 | 0.81 | 0.04 | 0.16 | 0.00 | 0.00 |
| 10717.52 | 7.3 | −10.5 | 3.5 | 41.8 | 0.73 | 0.04 | 0.23 | 0.00 | 0.00 |
| 10717.53 | 2.3 | −5.1 | 3.0 | 40.6 | 0.76 | 0.08 | 0.16 | 0.00 | 0.00 |
| 10717.62 | 0.7 | −5.6 | 5.2 | 40.1 | 0.65 | 0.04 | 0.31 | 0.00 | 0.00 |
| 10717.63 | 4.7 | −8.2 | 3.8 | 41.6 | 0.68 | 0.08 | 0.24 | 0.00 | 0.00 |
| 10717.71 | 5.7 | −8.4 | 3.0 | 41.0 | 0.55 | 0.00 | 0.45 | 0.00 | 0.00 |
| MoVNb | 0.00 | −1.4 | 1.8 | 40.9 | | | | | |
| 10717.72 | 6.5 | −10.5 | 4.3 | 40.5 | 0.58 | 0.04 | 0.39 | 0.00 | 0.00 |
| 10717.73 | −5.1 | 0.6 | 4.8 | 41.3 | 0.60 | 0.08 | 0.32 | 0.00 | 0.00 |
| 10615.41 | 2.7 | −6.1 | 3.8 | 40.3 | 0.70 | 0.00 | 0.30 | 0.00 | 0.00 |
| 10615.42 | 3.2 | −6.7 | 3.8 | 40.8 | 0.70 | 0.10 | 0.20 | 0.00 | 0.00 |
| 10615.51 | 1.6 | −3.8 | 2.5 | 39.5 | 0.60 | 0.00 | 0.40 | 0.00 | 0.00 |
| 10615.52 | 1.6 | −5.7 | 4.3 | 38.3 | 0.60 | 0.10 | 0.30 | 0.00 | 0.00 |
| 21122.21 | 4.6 | −8.6 | 4.3 | 39.4 | 0.84 | 0.01 | 0.15 | 0.00 | 0.00 |
| 21122.22 | 2.3 | −6.6 | 4.6 | 32.2 | 0.81 | 0.01 | 0.18 | 0.00 | 0.00 |
| 21122.23 | 4.0 | −7.7 | 4.0 | 39.6 | 0.78 | 0.01 | 0.21 | 0.00 | 0.00 |
| Blank | −0.3 | 0.2 | 0.4 | 0.0 | | | | | |
| 21122.24 | 4.8 | −9.4 | 4.9 | 40.3 | 0.75 | 0.01 | 0.24 | 0.00 | 0.00 |
| 21122.25 | 3.5 | −7.4 | 4.2 | 40.1 | 0.73 | 0.01 | 0.26 | 0.00 | 0.00 |
| 21122.13 | 4.7 | −9.2 | 4.7 | 39.9 | 0.79 | 0.00 | 0.21 | 0.00 | 0.00 |
| 21122.14 | 4.5 | −8.4 | 4.2 | 38.8 | 0.76 | 0.00 | 0.24 | 0.00 | 0.00 |
| 21122.31 | 4.6 | −8.2 | 3.9 | 38.9 | 0.83 | 0.02 | 0.15 | 0.00 | 0.00 |
| 21122.33 | 5.6 | −9.1 | 3.8 | 39.3 | 0.77 | 0.02 | 0.21 | 0.00 | 0.00 |
| 21122.42 | 4.8 | −8.4 | 3.9 | 39.1 | 0.79 | 0.03 | 0.18 | 0.00 | 0.00 |
| 21122.43 | 5.6 | −10.4 | 5.1 | 42.2 | 0.77 | 0.03 | 0.21 | 0.00 | 0.00 |
| 21123.1 | 6.2 | −10.6 | 4.7 | 40.6 | 0.69 | 0.00 | 0.31 | 0.00 | 0.00 |
| 21123.2 | 5.6 | −9.9 | 4.6 | 40.3 | 0.67 | 0.00 | 0.33 | 0.00 | 0.00 |
| 21123.3 | 5.6 | −9.1 | 3.8 | 42.0 | 0.65 | 0.00 | 0.35 | 0.00 | 0.00 |
| 21123.5 | 5.2 | −8.1 | 3.1 | 40.3 | 0.61 | 0.00 | 0.39 | 0.00 | 0.00 |
| 21123.7 | 5.6 | −8.2 | 2.9 | 40.3 | 0.59 | 0.00 | 0.41 | 0.00 | 0.00 |
| MoVNb | 2.1 | −3.4 | 1.6 | 41.9 | | | | | |
| 10652.31 | 8.7 | −12.6 | 4.2 | 41.7 | 0.80 | 0.00 | 0.20 | 0.00 | 0.00 |
| 10652.41 | 6.4 | −10.6 | 4.5 | 38.5 | 0.70 | 0.00 | 0.30 | 0.00 | 0.00 |
| 10652.61 | 3.7 | −5.9 | 2.5 | 39.7 | 0.50 | 0.00 | 0.50 | 0.00 | 0.00 |
| 10793.1 | 8.3 | −10.5 | 2.5 | 39.2 | 0.86 | 0.00 | 0.14 | 0.00 | 0.00 |
| 10793.3 | 8.1 | −10.4 | 2.6 | 39.1 | 0.81 | 0.00 | 0.19 | 0.00 | 0.00 |
| 10793.5 | 5.5 | −6.9 | 1.7 | 37.9 | 0.75 | 0.00 | 0.25 | 0.00 | 0.00 |

TABLE 47

Composition of Ni—Nb oxide mixtures

| | | 1 | 2 | 3 | 4 |
|---|---|---|---|---|---|
| | | Mole Fraction & Sample Mass, mg | | | |
| 1 | Ni | 0.8772 | 0.7692 | 0.6736 | 0.5882 |
| | Nb | 0.1228 | 0.2308 | 0.3264 | 0.4118 |
| | M | 17.1 | 36.9 | 39.3 | 36.5 |
| 2 | Ni | 0.8772 | 0.7692 | 0.6736 | 0.5882 |
| | Nb | 0.1228 | 0.2308 | 0.3264 | 0.4118 |
| | M | 37.4 | 37.2 | 40.3 | 39.0 |
| 3 | Ni | 0.8772 | 0.7692 | 0.6736 | 0.5882 |
| | Nb | 0.1228 | 0.2308 | 0.3264 | 0.4118 |
| | M | 42.1 | 42.4 | 48.3 | 41.0 |
| 4 | Ni | 0.8772 | 0.7692 | 0.6736 | 0.5882 |
| | Nb | 0.1228 | 0.2308 | 0.3264 | 0.4118 |
| | M | 50.3 | 39.3 | 38.0 | 39.7 |
| 5 | Ni | 0.8772 | 0.7692 | 0.6736 | 0.5882 |
| | Nb | 0.1228 | 0.2308 | 0.3264 | 0.4118 |
| | M | 37.8 | 39.1 | 48.9 | 50.4 |
| 6 | Ni | 0.8772 | 0.7692 | 0.6736 | 0.5882 |
| | Nb | 0.1228 | 0.2308 | 0.3264 | 0.4118 |
| | M | 36.6 | 38.3 | 39.0 | 40.4 |

TABLE 48

Ethane Conversion of Ni—Nb oxide mixtures listed in Table 47

| Precipitation Method | 1 | 2 | 3 | 4 |
|---|---|---|---|---|
| | | Ethane Conversion, % | | |
| 1  NH$_4$OH | 0.9 | 8.9 | 7.3 | 6.8 |
| 2  NEt$_4$OH | 8.9 | 6.2 | 8.6 | 11.4 |
| 3  K$_2$CO$_3$ | 0.0 | 0.0 | 0.0 | 0.1 |
| 4  NaOH | 0.3 | 2.4 | 3.6 | 4.2 |
| 5  KOH | 0.5 | 0.2 | 0.0 | 0.1 |
| 6  (NH$_4$)$_2$CO$_3$ | 10.7 | 11.2 | 11.4 | 10.5 |

TABLE 49

Ethylene Selectivity of Ni—Nb oxide mixtures listed in Table 47

| Precipitation Method | 1 | 2 | 3 | 4 |
|---|---|---|---|---|
| | | Ethylene Selectivity, % | | |
| 1  NH$_4$OH | 78.3 | 78.8 | 74.5 | 72.3 |
| 2  NEt$_4$OH | 82.4 | 88.0 | 88.1 | 83.1 |
| 3  K$_2$CO$_3$ | 0.0 | 50.1 | 27.3 | 0.0 |
| 4  NaOH | 3.4 | 15.0 | 21.8 | 21.8 |
| 5  KOH | 3.5 | 4.5 | 0.0 | 0.0 |
| 6  (NH$_4$)$_2$CO$_3$ | 80.7 | 82.6 | 87.1 | 83.6 |

TABLE 50

Composition and mass of Ni—Ta oxide mixtures; ethane conversion and ethylene selectivity

| | Mole Fraction & Sample Mass, mg | Ethane Conversion % | Ethylene Selectivity % |
|---|---|---|---|
| Ni | 0.50 | 8.1 | 87.8 |
| Ta | 0.50 | | |
| m | 81.8 | | |
| Ni | 0.55 | 8.0 | 89.5 |
| Ta | 0.45 | | |
| m | 59.2 | | |
| Ni | 0.61 | 8.6 | 86.6 |
| Ta | 0.39 | | |
| m | 55.8 | | |
| Ni | 0.67 | 7.9 | 85.8 |
| Ta | 0.33 | | |
| m | 41.5 | | |
| Ni | 0.74 | 8.8 | 86.9 |
| Ta | 0.26 | | |
| m | 41.4 | | |
| Ni | 0.81 | 9.5 | 87.4 |
| Ta | 0.19 | | |
| m | 43.3 | | |

What is claimed is:

1. A composition of matter comprising a material having the empirical formula $$Ni_xA_jB_kC_lO_i$$

wherein

Ni is nickel and x is in the range of about 0.5–0.96, with nickel being substantially in the oxidized state;

A is a combination of Nb and Ta and optionally Co and j is in the range of from about 0.04–0.8;

B is a dopant selected from the group consisting of Li, Na, K, Rb, Cs, Mg, Ca, Sr, Ba, Mn, La, Ce, Pr, Nd, Sm and combinations thereof and k is in the range of from 0–0.5;

C is a dopant selected from the group consisting of Sn, Al, Fe, Si, B, Sb, TR, In, Ge, Cr, Pb and combinations thereof and l is in the range of from 0–0.5;

i is a number that satisfies the valence requirements of the other elements present; and the sum of j, k and l is at least 0.04.

2. The composition of claim 1, wherein x is in the range of from about 0.5 to 0.8.

3. The composition of claim 1 wherein x is greater than 0.6.

4. The composition of claim 1 wherein j, k and l are each greater than zero and wherein the sum of j, k and l is smaller than 0.3.

5. A method comprising contacting a catalyst of claim 1 with one or more reactants to effect a reaction selected from the group consisting of dehydrogenation, selective oxidation, ammoxidation, amination, homo carbon-carbon coupling, cross carbon coupling, dimerization and isomerization.

6. The method of claim 5, wherein the reaction is dehydrogenation.

7. The method of claim 6, wherein the one or more reactants is an alkane selected from the group consisting of ethane, n-propane, i-propane, n-butane and isobutane.

8. A catalyst comprising:

a mixture of metal oxides having an empirical formula:

$$Ni_aCo_bNb_cTa_dSn_eK_fAl_gFe_hO_i;$$

wherein b, c and d are numbers greater than or equal to zero, but less than 0.5, and at least one of b, c and d is nonzero;

e and are numbers greater than or equal to zero, but less than or equal to 0.35;

g and h are numbers greater than or equal to zero, but less than or equal to 0.10;

a is a number greater than or equal to about 0.5, but less than one, and satisfies:

$$a>1-b-c-d-e-f-g-h;$$

and, i is a number that satisfies valence requirements, wherein if b is greater than zero, at least one of c, d, e, f, g or h is greater than zero.

9. The catalyst of claim 8, wherein:

c is greater than or equal to 0.10, but less than or equal to 0.50; and b, d, e, f, g, and h equal zero.

10. The catalyst of claim 9, wherein c is greater than or equal to 0.12, but less than or equal to 0.42.

11. The catalyst of claim 9, wherein c is greater than or equal to 0.14, but less than or equal to 0.25.

12. The catalyst of claim 9, wherein c is greater than or equal to 0.20, but less than or equal to 0.50.

13. The catalyst of claim 9, wherein c is greater than or equal to 0.31, but less than or equal to 0.41.

14. The catalyst of claim 8, wherein:

d is greater than or equal to 0.10, but less than or equal to 0.50; and b, c, e, f, g, and h equal zero.

15. The catalyst of claim 14, wherein d is greater than or equal to 0.19, but less than or equal to 0.50.

16. The catalyst of claim 14, wherein d is greater than or equal to 0.14, but less than or equal to 0.25.

17. The catalyst of claim 8, wherein:

b is greater than or equal to 0, but less than or equal to 0.20;

c is greater than or equal to 0, but less than or equal to 0.50; and d, e, f, g and h equal zero.

18. The catalyst of claim 17, wherein:

b is greater than or equal to 0.001, but less than or equal to 0.19; and c is greater than or equal to 0.02, but less than or equal to 0.499.

19. The catalyst of claim 17, wherein:

b is greater than or equal to 0, but less than or equal to 0.30; and c is greater than or equal to 0, but less than or equal to 0.45.

20. The catalyst of claim 19, wherein a is greater than or equal to 0.55, but less than or equal to 0.85.

21. The catalyst of claim 17, wherein:

b is greater than or equal to 0, but less than or equal to 0.20; and c is greater than or equal to 0, but less than or equal to 0.50.

22. The catalyst of claim 21, wherein:

b is less than or equal to 0.03; and c is less than or equal to 0.20, but less than or equal to 0.50.

23. The catalyst of claim 21, wherein:

b is less than or equal to 0.03; and c is less than or equal to 0.50.

24. The catalyst of claim 20, wherein c is greater than or equal to 0.15, but less than or equal to 0.26.

25. The catalyst of claim 21, wherein:

b is greater than or equal to 0.005, but less than or equal to 0.19; and c is greater than or equal to 0.13, but less than or equal to 0.33.

26. The catalyst of claim 25, wherein c is less than or equal to 0.23.

27. The catalyst of claim 8, wherein:

c is greater than or equal to 0, but less than or equal to 0.50;

d is greater than or equal to 0, but less than or equal to 0.50; and b, e, f, g and h equal zero.

28. The catalyst of claim 27, wherein:

c is greater than or equal to 0.03, but less than or equal to 0.40; and d is greater than or equal to 0.02, but less than or equal to 0.29.

29. The catalyst of claim 27, wherein:

a is greater than or equal to 0.50, but less than or equal to 0.87;

c is greater than or equal to 0.04, but less than or equal to 0.44; and d is greater than or equal to 0.04, but less than or equal to 0.44.

30. The catalyst of claim 29, wherein:

a is greater than or equal to 0.54, but less than or equal to 0.72;

c is greater than or equal to 0.04, but less than or equal to 0.38; and d is greater than or equal to 0.04, but less than or equal to 0.40.

31. The catalyst of claim 30, wherein:

a is less than or equal to 0.65;

c is less than or equal to 0.20; and d is greater than or equal to 0.15.

32. The catalyst of claim 8, wherein:

c, d and e are each greater than or equal to 0, but less than or equal to 0.35; and b, f, g and h equal zero.

33. The catalyst of claim 8, wherein:

c, d and f are each greater than or equal to 0, but less than or equal to 0.35; and b, e, g and h equal zero.

34. The catalyst of claim 33, wherein:

a is greater than or equal to 0.58, but less than or equal to 0.64;

c is greater than or equal to 0.06, but less than or equal to 0.38;

d is greater than or equal to 0.04, but less than or equal to 0.30; and f is less than or equal to 0.26.

35. The catalyst of claim 8, wherein:

a is greater than or equal to 0.55, but less than or equal to 0.65;

c is greater than or equal to 0.30, but less than or equal to 0.40; and b, d, e, and f equal zero.

36. The catalyst of claim 35, wherein:

a is greater than or equal to 0.58, but less than or equal to 0.61;

c is greater than or equal to 0.35, but less than or equal to 0.36;

g is greater than or equal to 0, but less than or equal to 0.05; and h is greater than or equal to 0, but less than or equal to 0.07.

37. A catalyst comprising:

a mixture of metal oxides having an empirical formula:

$$Ni_aCo_bNb_cTa_dSn_eK_fAl_gFe_hO_i;$$

wherein a is a number greater than or equal to 0.5, and less than 0.80, and satisfies:

$$a \leq 1-b-c-d-e-f-g-h$$

b is a number greater than or equal to zero, c and d are numbers each greater than zero, and the sum of b, c, and d ranges from 0.04 to about 0.50;

e and are numbers greater than or equal to zero, and less than or equal to 0.35;

g and h are numbers greater than or equal to zero, and less than or equal to 0.10; and, i is a number that satisfies valence requirements.

* * * * *

UNITED STATES PATENT AND TRADEMARK OFFICE
CERTIFICATE OF CORRECTION

PATENT NO. : 6,436,871 B1
DATED : August 20, 2002
INVENTOR(S) : Liu

It is certified that error appears in the above-identified patent and that said Letters Patent is hereby corrected as shown below:

Column 35,
Line 66, "TR," should be replaced with -- Tl --

Column 36,
Line 30, -- f -- should be inserted between "and" and "are"
Line 37, the formula "a > 1-b-c-d-e-f-g-h;" should be replaced with the formula
-- $a \leq 1-b-c-d-e-f-g-h$; --

Column 37,
Line 21, "0.03;" should be replaced with -- 0.10; --
Line 22, "c is less than" should be replaced with -- c is greater than --
Line 27, "20" should be replaced with -- 23 --

Column 38,
Line 55, -- f -- should be inserted between "and" and "are"

Signed and Sealed this

Eleventh Day of March, 2003

JAMES E. ROGAN
*Director of the United States Patent and Trademark Office*